United States Patent
Sharma et al.

(10) Patent No.: US 11,744,478 B2
(45) Date of Patent: Sep. 5, 2023

(54) ABSOLUTE INTRATHORACIC IMPEDANCE BASED SCHEME TO STRATIFY PATIENTS FOR RISK OF A HEART FAILURE EVENT

(71) Applicant: Medtronic, Inc., Minneapolis, MN (US)

(72) Inventors: Vinod Sharma, Maple Grove, MN (US); Jodi L. Redemske, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 942 days.

(21) Appl. No.: 16/511,932

(22) Filed: Jul. 15, 2019

(65) Prior Publication Data

US 2019/0350488 A1 Nov. 21, 2019

Related U.S. Application Data

(62) Division of application No. 15/222,461, filed on Jul. 28, 2016, now Pat. No. 10,368,774.
(Continued)

(51) Int. Cl.
*A61N 1/365* (2006.01)
*A61B 5/0537* (2021.01)
(Continued)

(52) U.S. Cl.
CPC .......... *A61B 5/0537* (2013.01); *A61B 5/0538* (2013.01); *A61B 5/7275* (2013.01);
(Continued)

(58) Field of Classification Search
CPC ... A61B 5/0537; A61B 5/0538; A61B 5/7275; A61N 1/36521; A61N 1/3702
See application file for complete search history.

(56) References Cited

U.S. PATENT DOCUMENTS

| 4,374,382 A | 2/1983 | Markowitz |
| 5,117,824 A | 6/1992 | Keimel et al. |

(Continued)

FOREIGN PATENT DOCUMENTS

| CN | 1867376 A | 11/2006 |
| CN | 102176861 A | 9/2011 |

(Continued)

OTHER PUBLICATIONS (PCT/US2016/044676) PCT Notification of Transmittal of the International Search Report and the Written Opinion of the International Searching Authority, dated Oct. 6, 2016, 12 pages.

*Primary Examiner* — Daniel L Cerioni

(57) ABSTRACT

A health care system acquires data determines whether a patient is at risk of hypervolemia or hypovolemia. The method comprises (a) acquiring from a device memory a patient's absolute intrathoracic impedance data over a pre-specified time period, (b) determining a running average of the intrathoracic impedance data over the pre-specified time period, and (c) determining by the system whether the running average of the intrathoracic impedance data over the pre-specified time period exceeds one of a first and second range, the first range being a higher value boundary of intrathoracic electrical impedance and the second range being a lower value boundary of intrathoracic electrical impedance.

12 Claims, 15 Drawing Sheets

Related U.S. Application Data

(60) Provisional application No. 62/199,057, filed on Jul. 30, 2015.

(51) Int. Cl.
    *A61B 5/0538*     (2021.01)
    *A61B 5/00*     (2006.01)
    *A61N 1/372*     (2006.01)
    *A61N 1/37*     (2006.01)

(52) U.S. Cl.
    CPC ....... *A61N 1/36521* (2013.01); *A61N 1/3702* (2013.01); *A61N 1/37258* (2013.01)

(56) References Cited

U.S. PATENT DOCUMENTS

| | | | |
|---|---|---|---|
| 5,545,186 | A | 8/1996 | Olson et al. |
| 5,755,736 | A | 5/1998 | Gillberg et al. |
| 7,553,937 | B2 | 6/2009 | Pau et al. |
| 7,986,994 | B2 | 7/2011 | Stadler |
| 8,052,611 | B2 | 11/2011 | Wariar et al. |
| 8,208,999 | B2 | 6/2012 | Wenzel et al. |
| 8,255,046 | B2 | 8/2012 | Sarkar et al. |
| 8,282,562 | B2 | 10/2012 | Koh |
| 8,428,718 | B2 | 4/2013 | Stadler et al. |
| 8,634,906 | B2 | 1/2014 | Wariar |
| 8,708,924 | B2 | 4/2014 | Wariar et al. |
| 9,113,789 | B2 | 8/2015 | Wenzel et al. |
| 9,138,151 | B2 | 9/2015 | Wariar et al. |
| 2005/0080460 | A1 | 4/2005 | Wang et al. |
| 2008/0161651 | A1 | 7/2008 | Peterson et al. |
| 2009/0062728 | A1 | 3/2009 | Woo et al. |
| 2009/0062730 | A1 | 3/2009 | Woo et al. |
| 2010/0030292 | A1 | 2/2010 | Sarkar |
| 2010/0069778 | A1 | 3/2010 | Bornzin et al. |
| 2010/0114204 | A1 | 5/2010 | Burnes et al. |
| 2011/0082084 | A1 | 4/2011 | Szeto et al. |
| 2011/0301491 | A1* | 12/2011 | Stadler ................. A61B 5/4875 600/547 |
| 2012/0059436 | A1 | 3/2012 | Fontaine et al. |
| 2012/0109243 | A1 | 5/2012 | Hettrick |
| 2012/0157856 | A1 | 6/2012 | An et al. |
| 2012/0172892 | A1 | 7/2012 | Grubac et al. |
| 2013/0030319 | A1 | 1/2013 | Hettrick et al. |
| 2013/0079646 | A1 | 3/2013 | Bhunia et al. |
| 2013/0084276 | A1 | 4/2013 | Watson et al. |
| 2013/0109944 | A1 | 5/2013 | Sparacino et al. |
| 2013/0116578 | A1 | 5/2013 | An et al. |
| 2013/0165802 | A1 | 6/2013 | Dalal et al. |
| 2013/0183681 | A1 | 7/2013 | McAleer |
| 2013/0197381 | A1 | 8/2013 | Charlton et al. |
| 2014/0128749 | A1 | 5/2014 | Sowelam |
| 2014/0274923 | A1 | 9/2014 | Sucharov et al. |
| 2014/0330090 | A1 | 11/2014 | Banet et al. |
| 2015/0289769 | A1 | 10/2015 | Ventatesh et al. |
| 2016/0038093 | A1 | 2/2016 | Sharma et al. |
| 2016/0198977 | A1 | 7/2016 | Eom et al. |
| 2016/0206250 | A1 | 7/2016 | Sharma et al. |
| 2016/0317073 | A1 | 11/2016 | Brockway et al. |
| 2016/0362362 | A1 | 12/2016 | Purohit et al. |
| 2017/0027474 | A1 | 2/2017 | Sharma et al. |

FOREIGN PATENT DOCUMENTS

| | | |
|---|---|---|
| CN | 102485172 B | 6/2012 |
| CN | 103998072 A | 8/2014 |
| CN | 104303061 A | 1/2015 |
| CN | 104644627 A | 5/2015 |
| CN | 104755930 A | 7/2015 |
| EP | 1455895 B1 | 9/2009 |
| EP | 1782068 B1 | 7/2010 |
| JP | 5871791 B2 | 10/2012 |
| WO | 2009/029899 A1 | 3/2009 |
| WO | 2011044927 A1 | 4/2011 |
| WO | 2016182511 A1 | 11/2016 |
| WO | 2017046203 A1 | 3/2017 |

\* cited by examiner

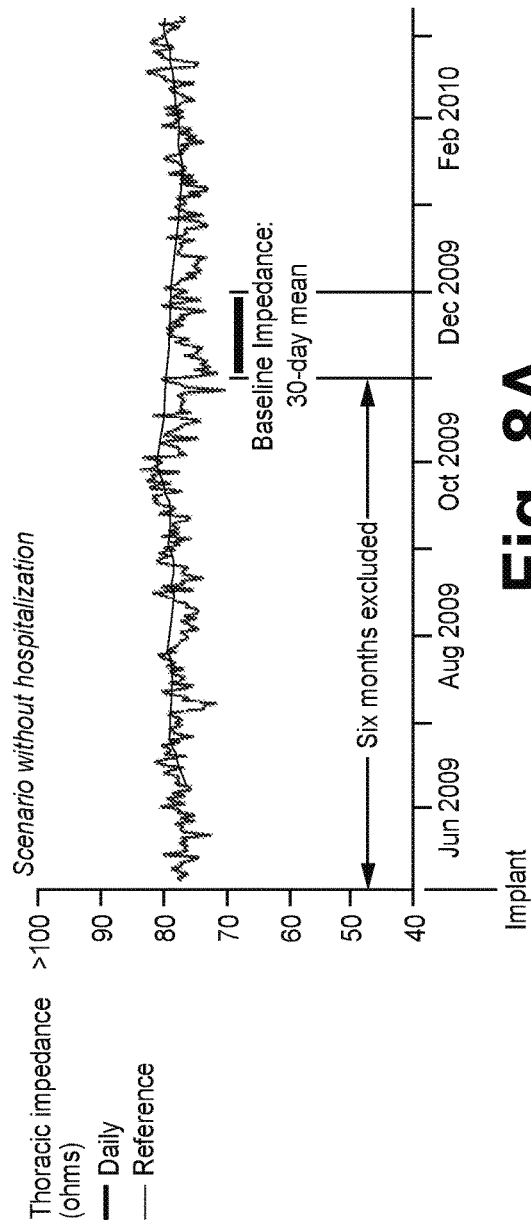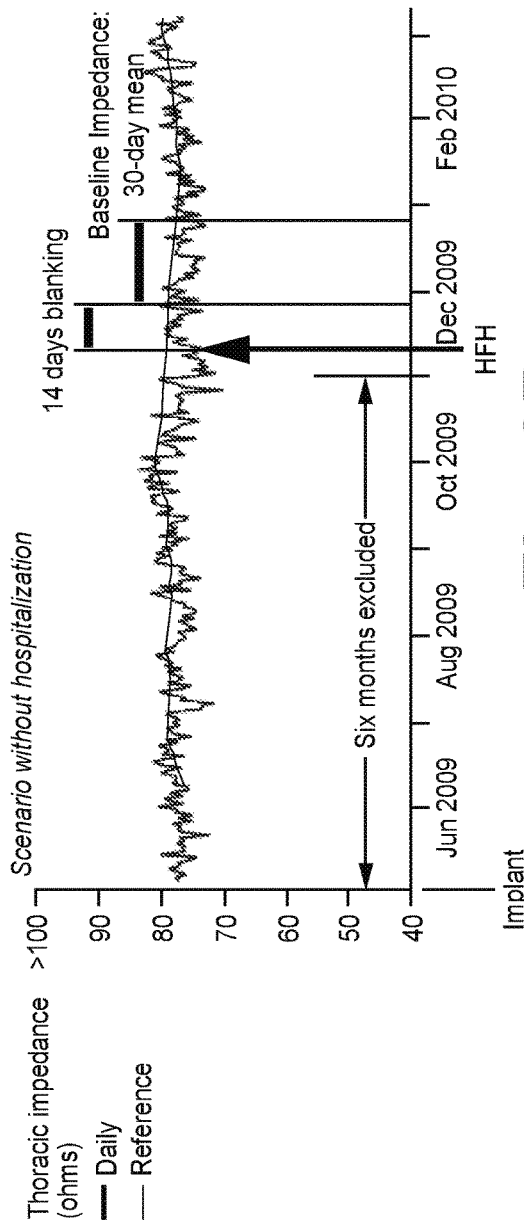

ABSOLUTE INTRATHORACIC IMPEDANCE BASED SCHEME TO STRATIFY PATIENTS FOR RISK OF A HEART FAILURE EVENT

CROSS-REFERENCE TO RELATED APPLICATIONS

This application claims the benefit of U.S. Provisional Application No. 62/199,057 filed on Jul. 30, 2015. The disclosure of the above application is incorporated herein by reference in its entirety.

TECHNICAL FIELD

The present disclosure relates to medical systems and medical devices, and, more particularly, to medical devices that monitor cardiac health.

BACKGROUND

Chronic heart failure (HF) occurs when a heart is unable to consistently pump blood at an adequate rate in response to the filling pressure. To improve the ability of the heart to pump blood, congestive heart failure patients, classified as having New York Heart Association (NYHA) class status of II to IV HF, may require implantable medical devices (IMDs) such as implantable cardioverter defibrillators (ICDs) and cardiac resynchronization therapy devices with defibrillation capability (CRT-Ds). Despite using IMDs to improve heart function, some HF patients may require hospitalization. Global health care systems incur billions of dollars each year due to heart failure hospitalizations (HFHs). Identifying patients at risk of a heart failure event (HFE) (e.g. HFH) to enable timely intervention and prevent expensive hospitalization remains a challenge. ICDs and CRT-Ds are configured to acquire data for a variety of diagnostic metrics that change with HF status and collectively have the potential to signal an increasing risk of HFE. Diagnostic parameter data collected by IMDs include activity, day and night heart rate, atrial tachycardia/atrial fibrillation (AT/AF) burden, mean rate during AT/AF, percent CRT pacing, number of shocks, and intrathoracic impedance. Additionally, preset or programmable thresholds for diagnostic metrics, when crossed, can trigger a notification, referred to as device observation. Each device observation is recorded in an IMD report and can be transmitted to an external healthcare system. Numerous healthcare systems (i.e. CARELINK® from Medtronic) are able to automatically notify health care workers of potential issues associated with a patient.

While numerous healthcare systems are able to automatically notify healthcare workers of potential health care issues such as that which is disclosed in US Patent Application US 2010-0030293 A1 to Sarkar et al., a health care system typically requires a physician's input to adjust therapy delivered to a patient. It is therefore desirable to store and transmit, in real-time, data to a system that is able to determine an increased heart failure (HF) event risk and is able to seamlessly respond to increased HF event risk.

In addition, impedance readings can include defined ranges such as hysteresis ranges as shown by U.S. Pat. No. 8,055,335 to Stylos, U.S. Pat. No. 8,700,143 to Stylos, but neither of these references determine whether a patient is dehydrated. It is also desirable to be able to predict in real-time risk of hypervolemia or hypovolemia in a patient. Hypervolemia occurs when too much fluid is present in the blood whereas hypovolemia (i.e. dehydration) occurs when too little fluid is present in the blood.

BRIEF DESCRIPTION OF DRAWINGS

FIG. 8A graphically depicts determining a baseline impedance average for a patient.

FIG. 8B graphically depicts determining patient's baseline impedance average as adjusted for a heart failure hospitalization that occurred within a pre-specified time period.

SUMMARY OF THE DISCLOSURE

Figure 1:
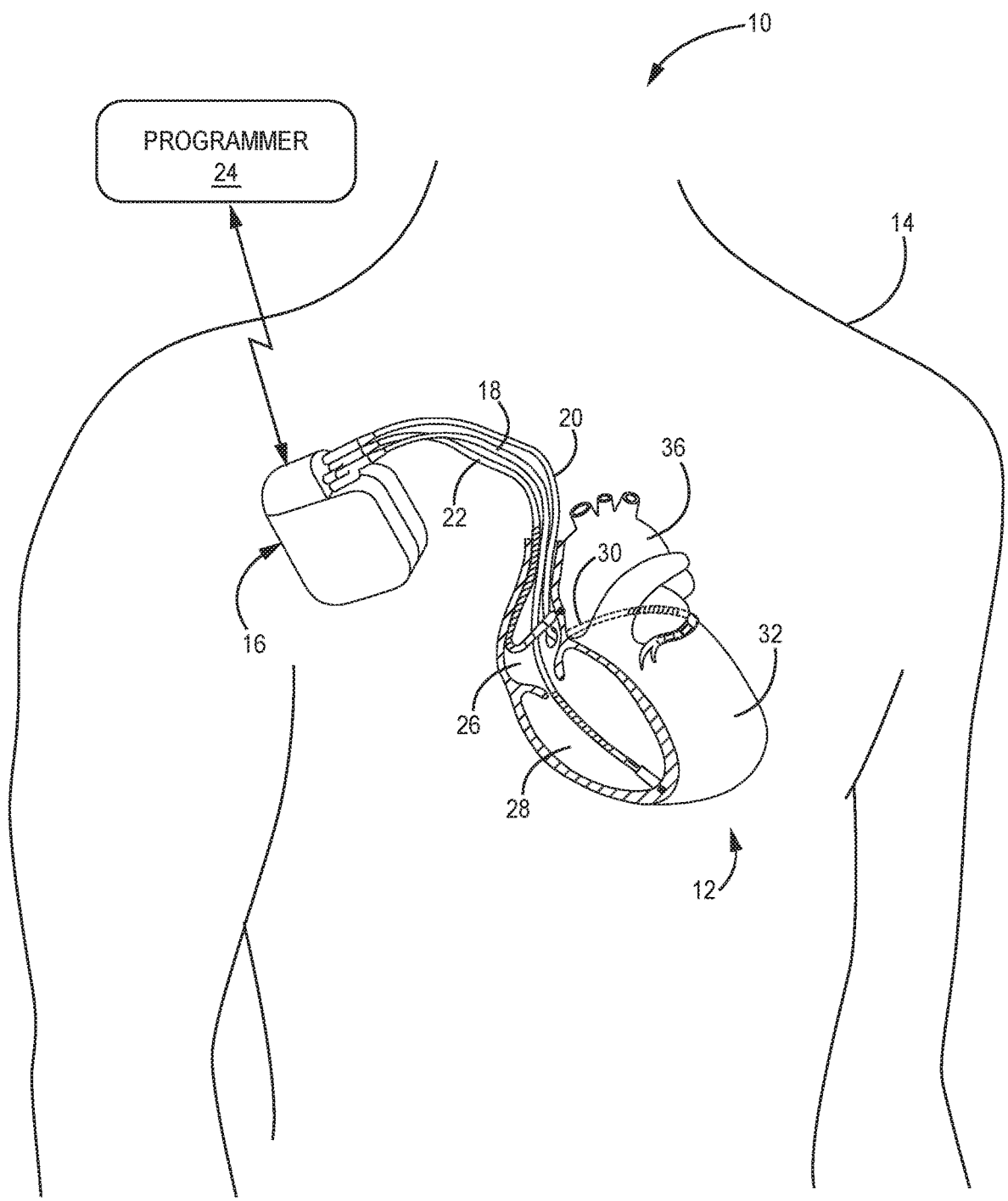
FIG. 1 is a conceptual drawing illustrating an example system configured to transmit diagnostic information indicative of heart failure that includes an implantable medical device (IMD) coupled to implantable medical leads.

Exemplary systems, methods, and interfaces described herein may be configured to operate a medical system for determining whether a patient is at risk of dehydration. Risk of dehydration (i.e. hypovolemia) is determined by acquiring from a device memory a patient's absolute intrathoracic impedance data over a pre-specified time period. A running average of the intrathoracic impedance data is then determined. The system then determines whether the running average of the intrathoracic impedance data exceeds either a first or a second range. The first range is a higher value boundary of intrathoracic electrical impedance while the second range is a lower value boundary of intrathoracic electrical impedance. A patient is dehydrated when the running average of intrathoracic impedance data exceeds the first range. The patient's therapy can then be adjusted in response to determining that the patient is dehydrated. In contrast, too low a value of intrathoracic electrical impedance (i.e. intrathoracic electrical impedance values lower than the second range) is indicative of hypervolemia.

In one or more other embodiments, data obtained from an IMD can also be used to predict heart failure event (e.g. heart failure hospitalization). In response to determining that a patient is experiencing deteriorating health, the health care system can automatically and seamlessly adjust therapy delivered to a patient. For example, the physician can pre-authorize certain stepped responses that are implemented without further input from the physician. Alternatively, the physician can be notified of a need to adjust therapy for the patient. The notification can be sent to the physician's personal digital assistant (e.g. cell phone, iPad, etc.) and the physician can quickly confirm that the adjusted therapy is agreed to by the physician.

The present disclosure achieves numerous benefits over conventional systems or techniques. For example, the present disclosure is able to determine in real-time whether the patient is at risk of hypervolemia or hypovolemia. In one or more other embodiments, a patients risk of a heart failure event can be determined, which allows the patient's treatment to be automatically adjusted in order to avoid or reduce the probability of a heart failure event.

DETAILED DESCRIPTION

Exemplary systems, methods, and interfaces shall be described with reference to FIGS. 1-14. It will be apparent to one skilled in the art that elements or processes from one embodiment may be used in combination with elements or processes of the other embodiments, and that the possible embodiments of such methods, apparatus, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

FIG. 1 is a conceptual drawing illustrating an example system 10 configured to transmit diagnostic information indicative of heart failure of patient 14. In the example of FIG. 1, system 10 includes IMD 16, which is coupled to leads 18, 20, and 22 and programmer 24. IMD 16 may be, for example, an implantable pacemaker, cardioverter, and/or defibrillator that provides electrical signals to heart 12 via electrodes coupled to one or more of leads 18, 20, and 22. Patient 14 is ordinarily, but not necessarily a human patient.

In general, the techniques described in this disclosure may be implemented by any medical device, e.g., implantable or external, that senses a signal indicative of cardiac activity, patient 14 activity, and/or fluid volume within patient 14. As one alternative example, the techniques described herein may be implemented in an external cardiac monitor that generates electrograms of heart 12 and detects thoracic fluid volumes, respiration, and/or cardiovascular pressure of patient 14.

In the example of FIG. 1, leads 18, 20, 22 extend into the heart 12 of patient 14 to sense electrical activity of heart 12 and/or deliver electrical stimulation to heart 12. Leads 18, 20, and 22 may also be used to detect a thoracic impedance indicative of fluid volume in patient 14, respiration rates, sleep apnea, or other patient metrics. Respiration metrics, e.g., respiration rates, tidal volume, and sleep apnea, may also be detectable via an electrogram, e.g., based on a signal component in a cardiac electrogram that is associated with respiration. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, system 10 may additionally or alternatively include one or more leads or lead segments (not shown in FIG. 1) that deploy one or more electrodes within the vena cava, or other veins. Furthermore, in some examples, system 10 may additionally or alternatively include temporary or permanent epicardial or subcutaneous leads with electrodes implanted outside of heart 12, instead of or in addition to transvenous, intracardiac leads 18, 20 and 22. Such leads may be used for one or more of cardiac sensing, pacing, or cardioversion/defibrillation. For example, these electrodes may allow alternative electrical sensing configurations that provide improved or supplemental sensing in some patients. In other examples, these other leads may be used to detect intrathoracic impedance as a patient metric for identifying a heart failure risk or fluid retention levels.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may detect arrhythmia of heart 12, such as tachycardia or fibrillation of the atria 26 and 36 and/or ventricles 28 and 32, and may also provide defibrillation therapy and/or cardioversion therapy via electrodes located on at least one of the leads 18, 20, 22. In some examples, IMD 16 may be programmed to deliver a progression of therapies, e.g., pulses with increasing energy levels, until a fibrillation of heart 12 is stopped. IMD 16 may detect fibrillation employing one or more fibrillation detection techniques known in the art.

In addition, IMD 16 may monitor the electrical signals of heart 12 for patient metrics stored in IMD 16 and/or used in generating the heart failure risk level. IMD 16 may utilize two of any electrodes carried on leads 18, 20, 22 to generate electrograms of cardiac activity. In some examples, IMD 16 may also use a housing electrode of IMD 16 (not shown) to generate electrograms and monitor cardiac activity. Although these electrograms may be used to monitor heart 12 for potential arrhythmias and other disorders for therapy, the electrograms may also be used to monitor the condition of heart 12. For example, IMD 16 may monitor heart rate (night time and day time), heart rate variability, ventricular or atrial intrinsic pacing rates, indicators of blood flow, or other indicators of the ability of heart 12 to pump blood or the progression of heart failure.

In some examples, IMD 16 may also use any two electrodes of leads 18, 20, and 22 or the housing electrode to sense the intrathoracic impedance of patient 14. As the tissues within the thoracic cavity of patient 14 increase in fluid content, the impedance between two electrodes may also change. For example, the impedance between an RV coil electrode and the housing electrode may be used to monitor changing intrathoracic impedance.

IMD 16 may use intrathoracic impedance to create a fluid index. As the fluid index increases, more fluid is being retained within patient 14 and heart 12 may be stressed to keep up with moving the greater amount of fluid. Therefore, this fluid index may be a patient metric transmitted in diagnostic data or used to generate the heart failure risk level. By monitoring the fluid index in addition to other patient metrics, IMD 16 may be able to reduce the number of false positive heart failure identifications relative to what might occur when monitoring only one or two patient metrics. Furthermore, IMD 16, along with other networked computing devices described herein, may facilitate remote monitoring of patient 14, e.g., monitoring by a health care professional when the patient is not located in a healthcare facility or clinic associated with the health care professional, during a post-hospitalization period. An example system for measuring thoracic impedance and determining a fluid index is described in U.S. Pat. No. 8,255,046 to Sarkar et al., entitled, "DETECTING WORSENING HEART FAILURE BASED ON IMPEDANCE MEASUREMENTS," which published on Feb. 4, 2010 and is incorporated herein by reference in its entirety.

IMD 16 may also communicate with external programmer 24. In some examples, programmer 24 comprises an external device, e.g., a handheld computing device, computer workstation, or networked computing device. Programmer 24 may include a user interface that receives input from a user. In other examples, the user may also interact with programmer 24 remotely via a networked computing device. The user may interact with programmer 24 to communicate with IMD 16. For example, the user may interact with programmer 24 to send an interrogation request and retrieve patient metrics or other diagnostic information from IMD 16. A user may also interact with programmer 24 to program IMD 16, e.g., select values for operational parameters of IMD 16. Although the user is a physician, technician, surgeon, electrophysiologist, or other healthcare professional, the user may be patient 14 in some examples.

For example, the user may use programmer 24 to retrieve information from IMD 16 regarding patient metric data and/or the heart failure risk level. Heart failure risk level may be transmitted as diagnostic information. Although programmer 24 may retrieve this information after submitting an interrogation request, IMD 16 may push or transmit the heart failure risk level, for example, if the heart failure risk level indicates a change in patient treatment is necessary.

IMD 16, external device 114, and/or programmer 24 may determine whether a patient is at risk of hypervolemia or hypovolemia. Additionally, the programmer 24 can determine the patient's HF event risk (e.g. HFH risk) level. A HF event is when a patient was admitted to the hospital for worsening HF or the patient has received Intravenous HF therapy (e.g. IV diuretics/vasodilators), ultrafiltration at any settings including an emergency department, ambulance, observation unit, urgent care, HF/Cardiology Clinic or the patient's home. Exemplary patient metric data may include intracardiac or intravascular pressure, activity, posture, respiration, thoracic impedance, impedance trend etc.

As another example, the user may use programmer 24 to retrieve information from IMD 16 regarding the performance or integrity of IMD 16 or other components of system 10, such as leads 18, 20 and 22, or a power source of IMD 16. In some examples, any of this information may be presented to the user as an alert (e.g., a notification or instruction). Further, alerts may be pushed from IMD 16 to facilitate alert delivery whenever programmer 24 is detectable by IMD 16. IMD 16 may wirelessly transmit alerts, or other diagnostic information, to facilitate immediate notification of the heart failure condition.

Programmer 24 may also allow the user to define how IMD 16 senses, detects, and manages each of the patient metrics. For example, the user may define the frequency of sampling or the evaluation window used to monitor the patient metrics. Additionally or alternatively, the user may use programmer 24 to set each metric threshold used to monitor the status of each patient metric. The metric thresholds may be used to determine when one or more patient metrics has reached a magnitude indicative of being at risk for heart failure and/or heart failure event. An example of such a method and/or system to predict risk of HF event (e.g. HFH) may be seen with respect to U.S. Provisional Application No. 62/024,285, filed on Jul. 14, 2014, U.S. Provisional Application No. 62/037,895, filed on Aug. 15, 2014 U.S. patent Ser. No. 14/798,225 filed on Jul. 13, 2015, entitled DETERMINING PROSPECTIVE RISK OF HEART FAILURE HOSPITALIZATION and assigned to the assignee of the present invention, the disclosure of each application is incorporated by reference in their entirety herein.

IMD 16 and programmer 24 may communicate via wireless communication using any techniques known in the art. Examples of communication techniques may include, for example, radiofrequency (RF) telemetry, but other communication techniques such as magnetic coupling are also contemplated. In some examples, programmer 24 may include a programming head that may be placed proximate to the body of the patient near the IMD 16 implant site in order to improve the quality or security of communication between IMD 16 and programmer 24.

IMD 16 may automatically detect each of the patient metrics and store them within the IMD for later transmission. Although IMD 16 may automatically detect a number (e.g. 10 or less) different patient metrics in some examples, IMD 16 may detect more or less patient metrics in other examples. For example, the patient metrics may include two or more of a thoracic fluid index, an atrial fibrillation duration, a ventricular contraction rate during atrial fibrillation, a patient activity, a nighttime heart rate, a heart rate variability, a cardiac resynchronization therapy (CRT) percentage (e.g., the percentage of cardiac cycles for which cardiac resynchronization pacing was provided), or the occurrence of or number of therapeutic electrical shocks. The metric-specific thresholds may include at least two of a thoracic fluid index threshold of approximately 60, an atrial fibrillation duration threshold of approximately 6 hours, a ventricular contraction rate threshold approximately equal to 90 beats per minute for 24 hours, a patient activity threshold approximately equal to 1 hour per day for seven consecutive days, a nighttime heart rate threshold of approximately 85 beats per minute for seven consecutive days, a heart rate variability threshold of approximately 40 milliseconds for seven consecutive days, a cardiac resynchronization therapy percentage threshold of 90 percent for five of seven consecutive days, or an electrical shock threshold of 1 electrical shock. In addition to transmitting diagnostic information during a pre-specified time period, IMD 16 may transmit diagnostic information to a clinician or other user prior to the hospitalization period. In other words, IMD 16 may transmit a heart failure risk level to a clinician before patient 14 is ever admitted to the hospital for a heart failure decompensation event. The risk level transmitted may be similar to the post-hospitalization risk level, but, in some examples, the risk level transmitted prior to hospitalization may be transmitted less frequently, in response to an interrogation request from the clinician or other user, or upon the risk level reaching a more severe level, e.g., a high or medium risk of hospitalization.

In addition, IMD 16 may alter the method with which patient metrics are stored within IMD 16. In other words, IMD 16 may store the automatically detected data observations with a dynamic data storage rate. Before patient 14 is admitted to the hospital, e.g., before HF event, the clinician or admitting healthcare professional may submit an interrogation request to IMD 16 in order to retrieve a portion of the stored patient metrics. The patient metrics may help the clinician determine if hospitalization of patient 14 is a prudent action for treatment. In response to the interrogation request, IMD 16 may transmit at least some of the automatically detected patient metrics stored in IMD 16.

Figure 2A:
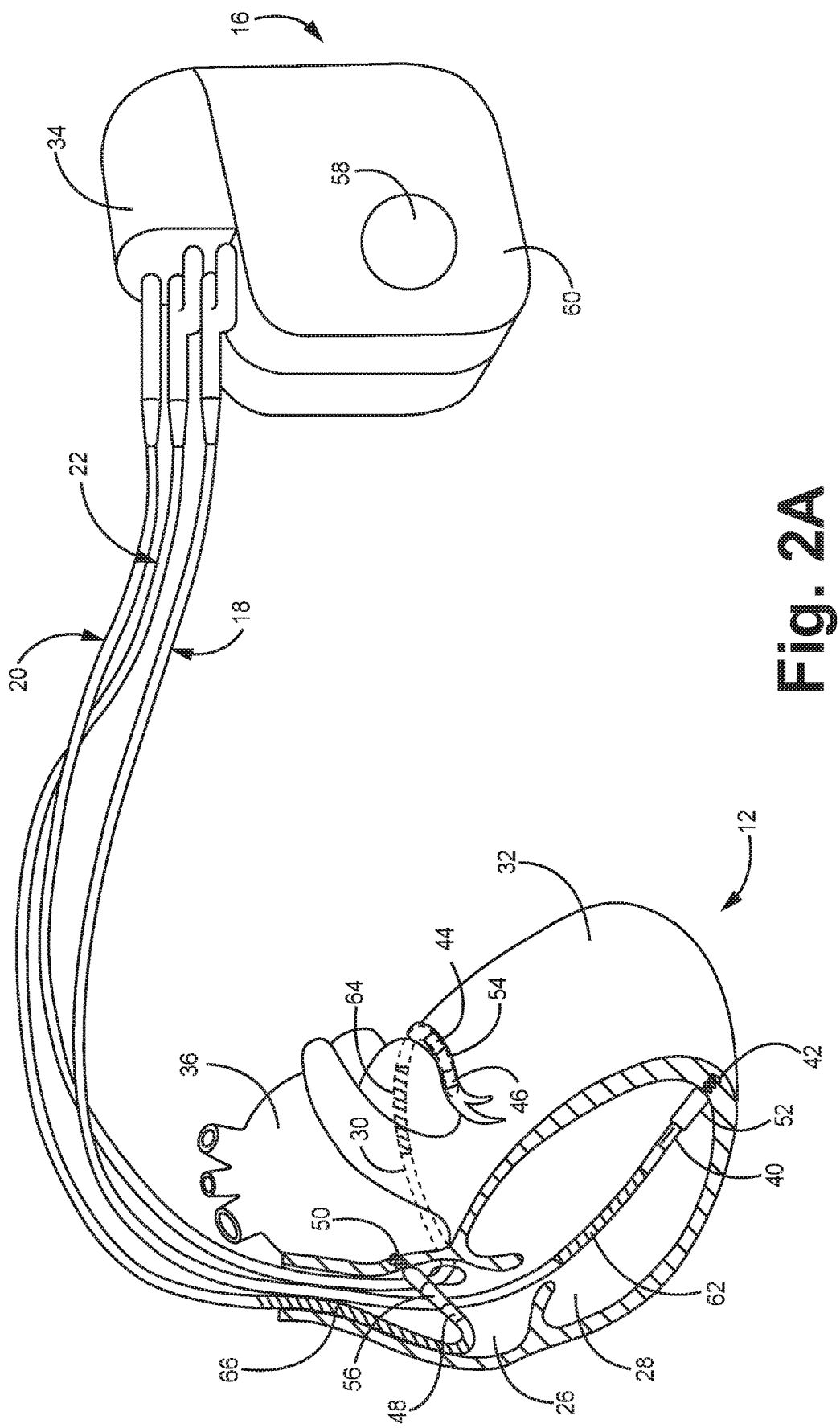
FIG. 2A is a conceptual drawing illustrating the example IMD and leads of FIG. 1 in conjunction with a heart.

FIG. 2A is a conceptual drawing illustrating IMD 16 and leads 18, 20, and 22 of system 10 in greater detail. As shown in FIG. 2A, IMD 16 is coupled to leads 18, 20, and 22. Leads 18, 20, 22 may be electrically coupled to a signal generator, e.g., stimulation generator, and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44, and 48 may take the form of ring electrodes, and electrodes 42, 46 and 50 may take the form of extendable helix tip electrodes mounted retractably within insulative electrode heads 52, 54 and 56, respectively. In other examples, one or more of electrodes 42, 46 and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64 and 66 may be electrically coupled to a respective one of the coiled conductors within the lead body of its associated lead 18, 20, 22, and thereby coupled to respective ones of the electrical contacts on the proximal end of leads 18, 20 and 22.

In some examples, as illustrated in FIG. 2A, IMD 16 includes one or more housing electrodes, such as housing electrode 58, which may be formed integrally with an outer surface of hermetically-sealed housing 60 of IMD 16, or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 3, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 58. The combination of electrodes used for sensing may be referred to as a sensing configuration or electrode vector.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes. The combination of electrodes used for delivery of stimulation or sensing, their associated conductors and connectors, and any tissue or fluid between the electrodes, may define an electrical path.

The configuration of system 10 illustrated in FIGS. 1 and 2A is merely one example. In other examples, a system may include epicardial leads and/or subcutaneous electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may sense electrical signals and/or deliver defibrillation pulses and other therapies to heart 12 via percutaneous leads that extend through the skin of patient 14 to a variety of positions within or outside of heart 12. Further, external electrodes or other sensors may be used by IMD 16 to deliver therapy to patient 14 and/or sense and detect patient metrics used to generate diagnostic information, e.g., a heart failure risk level, whether the patient has a running average of thoracic impedance within or outside the boundaries of the target thoracic impedance range.

Figure 2B:
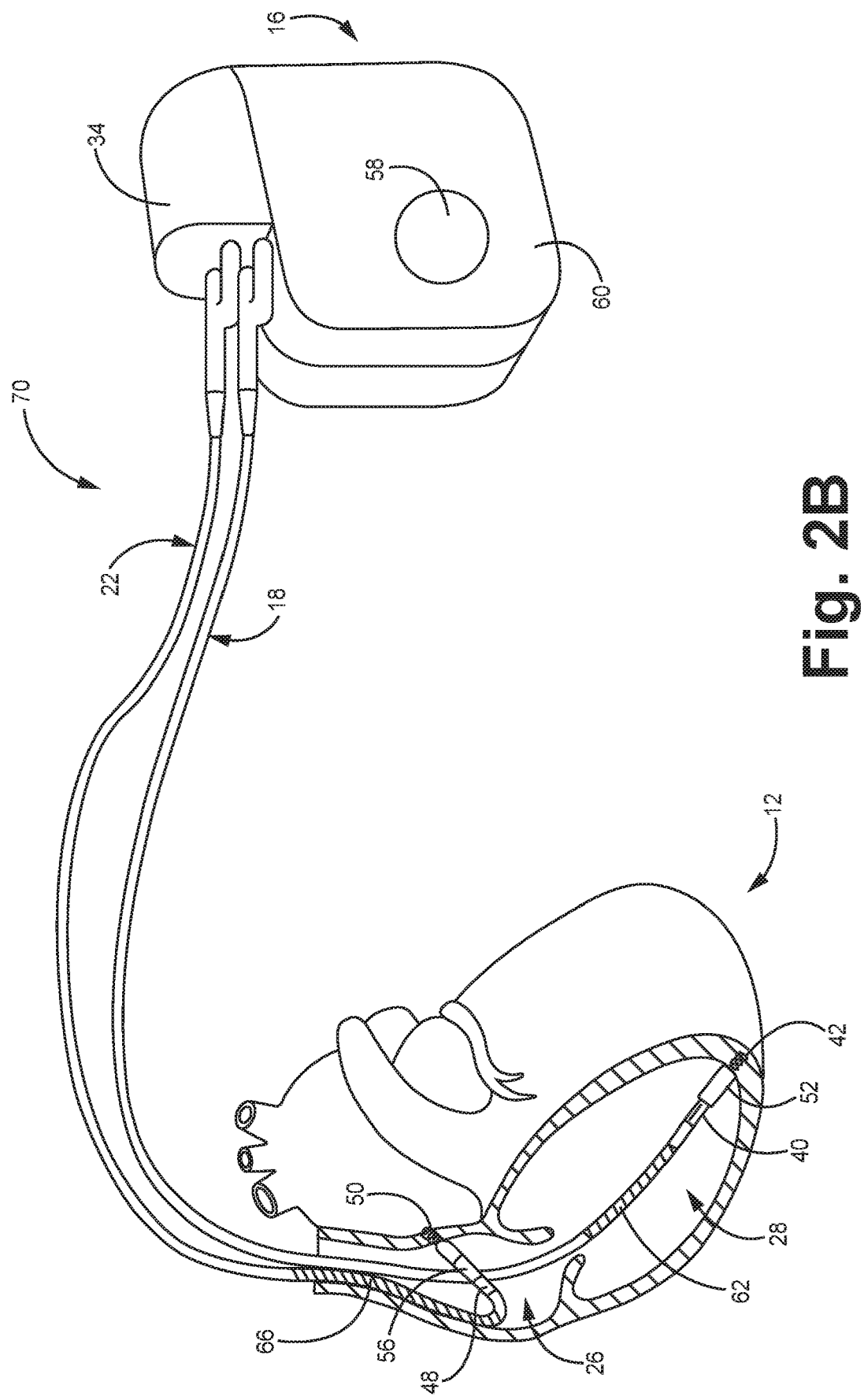
FIG. 2B is a conceptual drawing illustrating the example IMD of FIG. 1 coupled to a different configuration of implantable medical leads in conjunction with a heart.

In addition, in other examples, a system may include any suitable number of leads coupled to IMD 16, and each of the leads may extend to any location within or proximate to heart 12. For example, systems in accordance with this disclosure may include three transvenous leads located as illustrated in FIGS. 1 and 2, and an additional lead located within or proximate to left atrium 36. As another example, systems may include a single lead that extends from IMD 16 into right atrium 26 or right ventricle 28, or two leads that extend into a respective one of the right ventricle 26 and right atrium 26. An example of a two lead type of system is shown in FIG. 2B. Any electrodes located on these additional leads may be used in sensing and/or stimulation configurations.

Any of electrodes 40, 42, 44, 46, 48, 50, 62, 64, 66, and 58 may be utilized by IMD 16 to sense or detect patient metrics used to generate the heart failure risk level for patient 14. Typically, IMD 16 may detect and collect patient metrics from those electrode vectors used to treat patient 14. For example, IMD 16 may derive an atrial fibrillation duration, heart rate, and heart rate variability metrics from electrograms generated to deliver pacing therapy. However, IMD 16 may utilize other electrodes to detect these types of metrics from patient 14 when other electrical signals may be more appropriate for therapy.

In addition to electrograms of cardiac signals, any of electrodes 40, 42, 44, 46, 48, 50, 62, 64, 66, and 58 may be used to sense non-cardiac signals. For example, two or more electrodes may be used to measure an impedance within the thoracic cavity of patient 14. Intrathoracic impedance may be used to generate a fluid index patient metric that indicates the amount of fluid building up within patient 14. Since a greater amount of fluid may indicate increased pumping loads on heart 12, the fluid index may be used as an indicator of HFH risk. IMD 16 may periodically measure the intrathoracic impedance to identify a trend in the fluid index over days, weeks, months, and even years of patient monitoring. In general, the two electrodes used to measure the intrathoracic impedance may be located at two different positions within the chest of patient 14. For example, coil electrode 62 and housing electrode 58 may be used as the sensing vector for intrathoracic impedance because electrode 62 is located within RV 28 and housing electrode 58 is located at the IMD 16 implant site generally in the upper chest region. However, other electrodes spanning multiple organs or tissues of patient 14 may also be used, e.g., an additional implanted electrode used only for measuring thoracic impedance.

FIG. 2B is a conceptual diagram illustrating another example system 70, which is similar to system 10 of FIGS. 1 and 2A, but includes two leads 18, 22, rather than three leads. Leads 18, 22 are implanted within right ventricle 28 and right atrium 26, respectively. System 70 shown in FIG. 2B may be useful for physiological sensing and/or providing pacing, cardioversion, or other therapies to heart 12. Detection of patient diagnostic data according to this disclosure may be performed in two lead systems in the manner described herein with respect to three lead systems. In other examples, a system similar to systems 10 and 70 may only include one lead (e.g., any of leads 18, 20 or 22) to deliver therapy and/or sensor and detect patient metrics related to monitoring risk of heart failure. Alternatively, diagnostic data may be implemented in systems utilizing subcutaneous leads, subcutaneous IMDs, or even external medical devices. Although FIGS. 1-2 provide some useful IMD 16 implantation examples, skilled artisans appreciate that IMD 16 and its associated electrodes can be implanted in other locations of the body and can include leads or be leadless.

Figure 3:
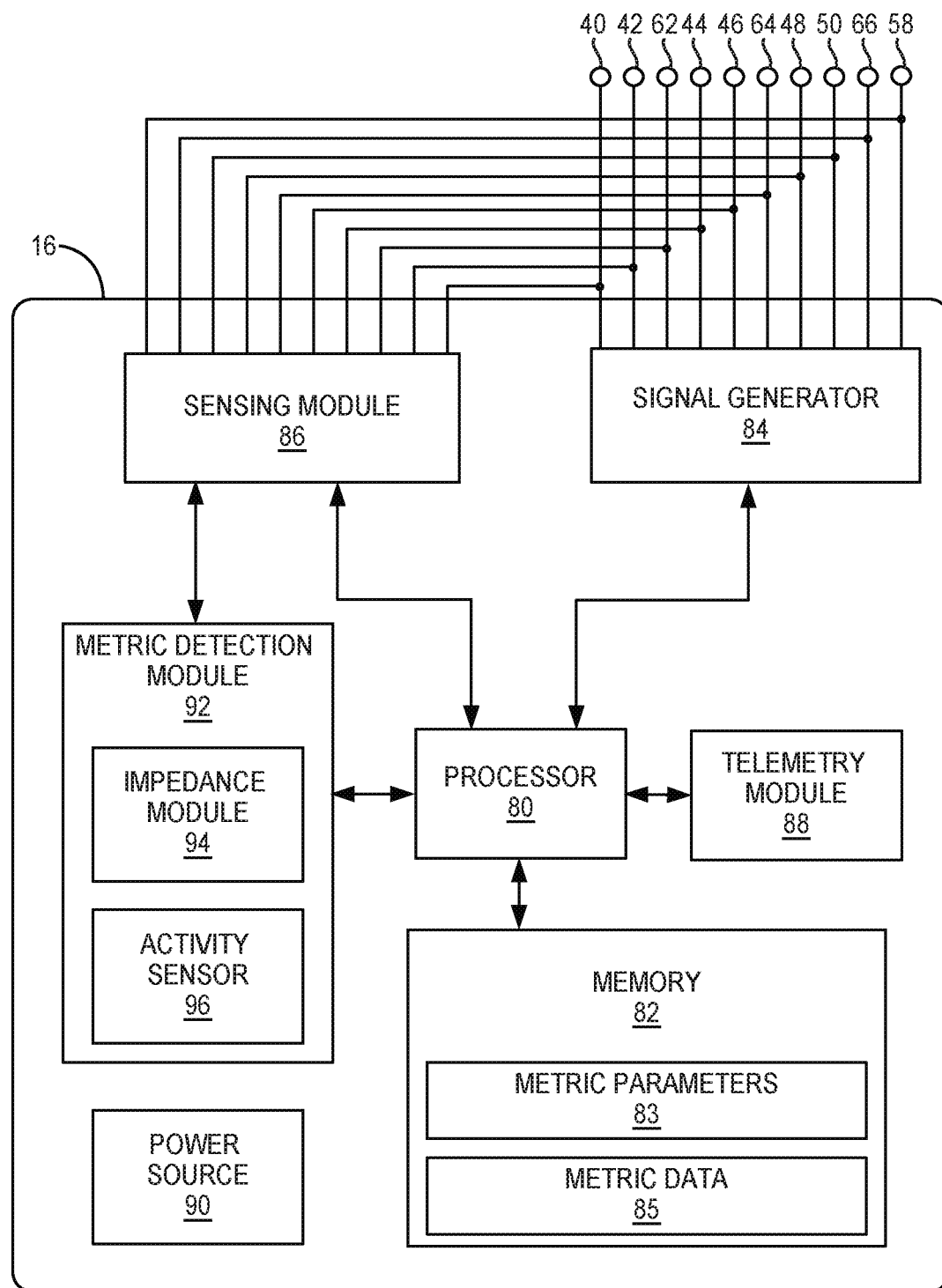
FIG. 3 is a functional block diagram illustrating an example configuration of the IMD of FIG. 1.

FIG. 3 is a functional block diagram illustrating an example configuration of IMD 16. In the illustrated example, IMD 16 includes a processor 80, memory 82, metric detection module 92, signal generator 84, sensing module 86, telemetry module 88, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver stimulation therapy to heart 12 according to a therapy parameters, which may be stored in memory 82. For example, processor 80 may control signal generator 84 to deliver electrical pulses with the amplitudes, pulse widths, frequency, or electrode polarities specified by the therapy parameters.

Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. In the illustrated example, signal generator 84 is configured to generate and deliver electrical stimulation therapy to heart 12. For example, signal generator 84 may deliver defibrillation shocks to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Electrical sensing module 86 monitors signals from at least one of electrodes 40, 42, 44, 46, 48, 50, 58, 62, 64 or 66 in order to monitor electrical activity of heart 12, impedance, or other electrical phenomenon. Sensing may be done to determine heart rates or heart rate variability, or to detect arrhythmias or other electrical signals. Sensing module 86 may also include a switch module to select which of the available electrodes are used to sense the heart activity, depending upon which electrode combination, or electrode vector, is used in the current sensing configuration. In some examples, processor 80 may select the electrodes that function as sense electrodes, i.e., select the sensing configuration, via the switch module within sensing module 86. Sensing module 86 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 80, e.g., as described in U.S. Pat. No.

5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processor 80 may control the functionality of sensing module 86 by providing signals via a data/address bus.

Processor 80 may include a timing and control module, which may be embodied as hardware, firmware, software, or any combination thereof. The timing and control module may comprise a dedicated hardware circuit, such as an ASIC, separate from other processor 80 components, such as a microprocessor, or a software module executed by a component of processor 80, which may be a microprocessor or ASIC. The timing and control module may implement programmable counters. If IMD 16 is configured to generate and deliver pacing pulses to heart 12, such counters may control the basic time intervals associated with DDD, VVI, DVI, VDD, AAI, DDI, DDDR, VVIR, DVIR, VDDR, AAIR, DDIR, CRT, and other modes of pacing.

Intervals defined by the timing and control module within processor 80 may include atrial and ventricular pacing escape intervals, refractory periods during which sensed P-waves and R-waves are ineffective to restart timing of the escape intervals, and the pulse widths of the pacing pulses. As another example, the timing and control module may withhold sensing from one or more channels of sensing module 86 for a time interval during and after delivery of electrical stimulation to heart 12. The durations of these intervals may be determined by processor 80 in response to stored data in memory 82. The timing and control module of processor 80 may also determine the amplitude of the cardiac pacing pulses.

Interval counters implemented by the timing and control module of processor 80 may be reset upon sensing of R-waves and P-waves with detection channels of sensing module 86. In examples in which IMD 16 provides pacing, signal generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. In such examples, processor 80 may reset the interval counters upon the generation of pacing pulses by signal generator 84, and thereby control the basic timing of cardiac pacing functions, including anti-tachyarrhythmia pacing.

The value of the count present in the interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to detect a tachyarrhythmia event, such as atrial fibrillation (AF), atrial tachycardia (AT), ventricular fibrillation (VF), or ventricular tachycardia (VT). These intervals may also be used to detect the overall heart rate, ventricular contraction rate, and heart rate variability. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies may also be employed by processor 80 in other examples.

In some examples, processor 80 may determine that tachyarrhythmia has occurred by identification of shortened R-R (or P-P) interval lengths. Generally, processor 80 detects tachycardia when the interval length falls below 220 milliseconds (ms) and fibrillation when the interval length falls below 180 ms. These interval lengths are merely examples, and a user may define the interval lengths as desired, which may then be stored within memory 82. This interval length may need to be detected for a certain number of consecutive cycles, for a certain percentage of cycles within a running window, or a running average for a certain number of cardiac cycles, as examples.

In the event that processor 80 detects an atrial or ventricular tachyarrhythmia based on signals from sensing module 86, and an anti-tachyarrhythmia pacing regimen is desired, timing intervals for controlling the generation of anti-tachyarrhythmia pacing therapies by signal generator 84 may be loaded by processor 80 into the timing and control module to control the operation of the escape interval counters therein and to define refractory periods during which detection of R-waves and P-waves is ineffective to restart the escape interval counters for the an anti-tachyarrhythmia pacing. Processor 80 detects data (e.g. data observations etc.) at an IMD16 check and/or interrogation time point. Data is sensed based on signals from sensing module 86. Additionally, cardioversion or defibrillation shock can be determined to be needed based upon sensed data, and processor 80 may control the amplitude, form and timing of the shock delivered by signal generator 84.

Memory 82 is configured to store data. Exemplary data can be associated with a variety of operational parameters, therapy parameters, sensed and detected data, and any other information related to the therapy and treatment of patient 14. In the example of FIG. 3, memory 82 also includes metric parameters 83 and metric data 85. Metric parameters 83 may include all of the parameters and instructions required by processor 80 and metric detection module 92 to sense and detect each of the patient metrics used to generate the diagnostic information transmitted by IMD 16. Metric data 85 may store all of the data generated from the sensing and detecting of each patient metric. In this manner, memory 82 stores a plurality of automatically detected patient metrics as the data required to generate a risk level of patient 14 being admitted to the hospital due to heart failure.

Metric parameters 83 may include definitions of each of the patient metrics automatically sensed or measured by metric detection module 92. These definitions may include instructions regarding what electrodes or sensors to use in the detection of each metric. Preferred metrics include an (1) impedance trend index (also referred to as OPTIVOL® commercially available in IMDs from Medtronic Inc., located in MN), (2) intrathoracic impedance, (3) atrial tachycardia/atrial fibrillation (AT/AF) burden, (4) mean ventricular rate during AT/AF, (5) patient activity, (6) V rate, (7) day and night heart rate, (8) percent CRT pacing, and/or (9) number of shocks. OPTIVOL® is described with respect to U.S. patent Ser. No. 10/727,008 filed on Dec. 3, 2003 issued as U.S. Pat. No. 7,986,994, and assigned to the assignee of the present invention, the disclosure of which is incorporated by reference in its entirety herein. Other suitable metrics can also be used. For example, a reference or baseline level impedance is established for a patient from which subsequently acquired raw impedance data is compared. For example, raw impedance can be acquired from the electrodes (e.g. RV coil to Can) and compared to the reference impedance (also referred to as normal impedance or baseline impedance. Baseline impedance can be derived by averaging impedance over a duration of 7 days (1-week) to 90 days (3-months).

Metric parameters 83 may also store a metric-specific threshold for each of the patient metrics automatically detected by metric detection module 92. Metric thresholds may be predetermined and held constant over the entire monitoring of patient 14. In some examples, however, metric thresholds may be modified by a user during therapy or processor 80 may automatically modify one or more metric thresholds to compensate for certain patient conditions. For example, a heart rate threshold may be changed over the course of monitoring if the normal or baseline heart rate has changed during therapy.

In one example, these metric-specific thresholds may include a thoracic fluid index threshold of approximately 60, an atrial fibrillation burden threshold of approximately 6 consecutive hours, a ventricular contraction rate threshold approximately equal to 90 beats per minute for 24 hours, a patient activity threshold approximately equal to 1 hour per day for seven consecutive days, a nighttime heart rate threshold of approximately 85 beats per minute for seven consecutive days, a heart rate variability threshold of approximately 40 milliseconds for seven consecutive days, a cardiac resynchronization therapy percentage threshold of 90 percent for five of seven consecutive days, and an electrical shock number threshold of 1 electrical shock. These thresholds may be different in other examples, and may be configured by a user, e.g., a clinician, for an individual patient.

Processor 80 may alter the method with which patient metrics are stored in memory 82 as metric data 85. In other words, processor 80 may store the automatically detected patient metrics with a dynamic data storage rate. Metric detection module 92 may, for example, transmit diagnostic data that is based on the patient metrics and whether any of the metrics exceed the respective specific metric thresholds. Any time that an automatically detected patient metric exceeds their respective metric threshold, the patient metric can be counted.

In this manner, metric detection module 92 may automatically detect each of the patient metrics and store them within metric data 85 for later transmission.

Example fluid index values and impedance measurements are described in U.S. Patent Application No. 2010/0030292 entitled "DETECTING WORSENING HEART FAILURE BASED ON IMPEDANCE MEASUREMENTS," which is incorporated by reference herein in its entirety. As the intrathoracic impedance remains low, the fluid index may increase. Conversely, as the intrathoracic impedance remains high, the fluid index may decrease. In this manner, the fluid index value maybe a numerical representation of retained fluid that is specific to patient 14. In other examples, the intrathoracic impedance may be alternatively used.

Metric data 85 is a portion of memory 82 that may store some or all of the patient metric data that is sensed and/or detected by metric detection module 92. Metric data 85 may store the data for each metric on a rolling basis during an evaluation window. The evaluation window may only retain recent data and delete older data from the evaluation window when new data enters the evaluation window. In this manner, the evaluation window may include only recent data for a predetermined period of time. In one or more other embodiments, memory can be configured for long term storage of data. Processor 80 may access metric data when necessary to retrieve and transmit patient metric data and/or generate heart failure risk levels. In addition, metric data 85 may store any and all data observations, heart failure risk levels or other generated information related to the heart failure risk of patient 14. The data stored in metric data 85 may be transmitted as part of diagnostic information. Although metric parameters 83 and/or metric data 85 may consist of separate physical memories, these components may simply be an allocated portion of the greater memory 82.

Metric detection module 92 may automatically sense and detect each of the patient metrics. Metric detection module 92 may then generate diagnostic data, e.g., data that indicates a threshold has been crossed, risk levels, based on the patient metrics. For example, metric detection module 92 may measure the thoracic impedance, analyze an electrogram of heart 12, monitor the electrical stimulation therapy delivered to patient 14, or sense the patient activity. It is noted that functions attributed to metric detection module 92 herein may be embodied as software, firmware, hardware or any combination thereof. In some examples, metric detection module 92 may at least partially be a software process executed by processor 80. Metric detection module 92 may sense or detect any of the patient metrics used as a basis for generating the heart failure risk level or otherwise indication of heart failure status or that patient 14 is at risk for hospitalization. In one example, metric detection module 92 may compare each of the patient metrics to their respective metric-specific thresholds defined in metric parameters 83 to generate the heart failure risk level. Metric detection module 92 may automatically detect two or more patient metrics. In other examples, metric detection module 92 may detect different patient metrics.

In one example, metric detection module 92 may analyze electrograms received from sensing module 86 to detect an atrial fibrillation or atrial tachycardia, and determine atrial tachycardia or fibrillation burden, e.g., duration, as well as a ventricular contraction rate during atrial fibrillation. Metric detection module 92 may also analyze electrograms in conjunction with a real-time clock, patient posture or activity signal, e.g., from activity sensor 96, and/or other physiological signals indicative of when a patient is asleep or awake to determine a nighttime (or sleeping) heart rate or a daytime (or awake) heart rate or a difference between the day and night heart rate, and also analyze electrograms to determine a heart rate variability, or any other detectable cardiac events from one or more electrograms. As described above, metric detection module 92 may use peak detection, interval detection, or other methods to analyze the electrograms.

In addition, metric detection module 92 may include and/or control impedance module 94 and activity sensor 96. Impedance module 94 may be used to detect the thoracic impedance used to generate the thoracic fluid index. As described herein, impedance module 94 may utilize any of the electrodes of FIG. 1, 2 or 3 to take intrathoracic impedance measurements. In other examples, impedance module 94 may utilize separate electrodes coupled to IMD 16 or in wireless communication with telemetry module 88. Once impedance module 94 measures the intrathoracic impedance of patient 14, metric detection module 92 may generate the thoracic fluid index and compare the index to the thoracic fluid index threshold defined in metric parameters 83.

Activity sensor 96 may include one or more accelerometers or other devices capable of detecting motion and/or position of patient 14. Activity sensor 96 may therefore detect activities of patient 14 or postures engaged by patient 14. Metric detection module 92 may, for example, monitor the patient activity metric based on the magnitude or duration of each activity and compare the determined metric data to the activity threshold defined in metric parameters 83. In addition to detecting events of patient 14, metric detection module 92 may also detect certain therapies delivered by signal generator 84, e.g., as directed by processor 80. Metric detection module 92 may monitor signals through signal generator 84 or receive therapy information directly from processor 80 for the detection. Example patient metrics detected by this method may include a cardiac resynchronization therapy percentage or metrics related to delivery of electrical shocks.

The cardiac resynchronization therapy (CRT) metric may be the amount or percentage of time each day, or an amount of percentage of cardiac cycles, as examples, that IMD 16 delivers cardiac resynchronization therapy to heart 12. Low CRT amounts or percentages may indicate that beneficial therapy is not being effectively delivered and that adjustment of therapy parameters, e.g., an atrioventricular delay or a lower pacing rate, may improve therapy efficacy. In one example, higher CRT amounts or percentages may indicate that heart 12 is sufficiently pumping blood through the vasculature with the aid of therapy to prevent fluid buildup. In examples of other types of cardiac pacing (non-CRT) or stimulation therapy, higher therapy percentages may indicate that heart 12 is unable to keep up with blood flow requirements.

An electrical shock may be a defibrillation event or other high energy shock used to return heart 12 to a normal rhythm. The metric related electrical shocks may be a number or frequency of electrical shocks, e.g., a number of shocks within a period of time. Metric detection module 92 may detect these patient metrics as well and compare them to a cardiac resynchronization therapy percentage and shock event threshold, respectively, defined in metric parameters 83 to determine when each patient metric has become critical. In one example, the electrical shock event metric may become critical when a threshold number of shocks is delivered, e.g., within a time period, or even when patient 14 even receives one therapeutic shock.

Metric detection module 92 may include additional sub-modules or sub-routines that detect and monitor other patient metrics used to monitor patient 14 and/or generate the HF event (e.g. HFH) risk level. In some examples, metric detection module 92, or portions thereof, may be incorporated into processor 80 or sensing module 86. In other examples, raw data used to produce patient metric data may be stored in metric data 85 for later processing or transmission to an external device. An external device may then produce each patient metric from the raw data, e.g., electrogram or raw intrathoracic impedance which is subsequently compared to a reference impedance. In other examples, metric detection module 92 may additionally receive data from one or more implanted or external devices used to detect each metric which IMD 16 may store as metric data.

In some examples, the patient metric thresholds used to generate the risk levels may change over time, e.g., the patient metric thresholds may either be modified by a user or automatically changed based on other patient conditions. Telemetry module 88 may receive commands from programmer 24, for example, to modify one or more metric parameters 83 (e.g., metric creation instructions or metric-specific thresholds). In some examples, processor 80 may automatically adjust a metric-specific threshold if certain conditions are present in patient 14. For example, the threshold may be adjusted if patient 14 is experiencing certain arrhythmias or data contained in cardiac electrograms change, e.g., there is a deviation in ST elevations or presence of pre-ventricular contractions, in such a manner that requires a change in the threshold.

Processor 80 may generate risk levels (e.g. risk of, or exhibiting hypervolemia, hypovolemia, HF event risk level, HFH risk level) based upon the patient metrics sensed, detected, and stored in metric data 85 of memory 82. For example, processor 80 may continually update the risk level as metric detection module 92 updates each patient metric. In other examples, processor 80 may periodically update the HFH risk level according to an updating schedule. In one or more other embodiments, the total number of data observations that exceed a threshold within a pre-specified period of time can be used to determine the risk of heart failure hospitalization.

As described above, processor 80 may provide an alert to a user, e.g., of programmer 24, regarding the data from any patient metric and/or the HF event risk level. In one example, processor 80 may provide an alert with the HFH risk level when programmer 24 or another device communicates with IMD 16. Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals, e.g., EGMs, produced by atrial and ventricular sense amplifier circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac events that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

In some examples, IMD 16 may signal programmer 24 to further communicate with and pass the alert through a network such as the Medtronic CareLink® Network developed by Medtronic, Inc., of Minneapolis, Minn., or some other network linking patient 14 to a clinician. In this manner, a computing device or user interface of the network may be the external computing device that delivers the alert, e.g., patient metric data. In other examples, one or more steps in the generation of the heart failure risk level may occur within a device external of patient 14, e.g., within programmer 24 or a server networked to programmer 24. In this manner, IMD 16 may detect and store patient metrics before transmitting the patient metrics to a different computing device.

In addition to transmitting diagnostic information, processor 80 may control telemetry module 88 to transmit diagnostic information to a clinician or other user. If one of the automatically detected patient metrics exceeds its respective metric-specific threshold, processor 80 may control telemetry module to transmit that patient metric and possibly other patient metrics to allow the clinician to more accurately diagnose the problem with patient 14.

Figure 4:
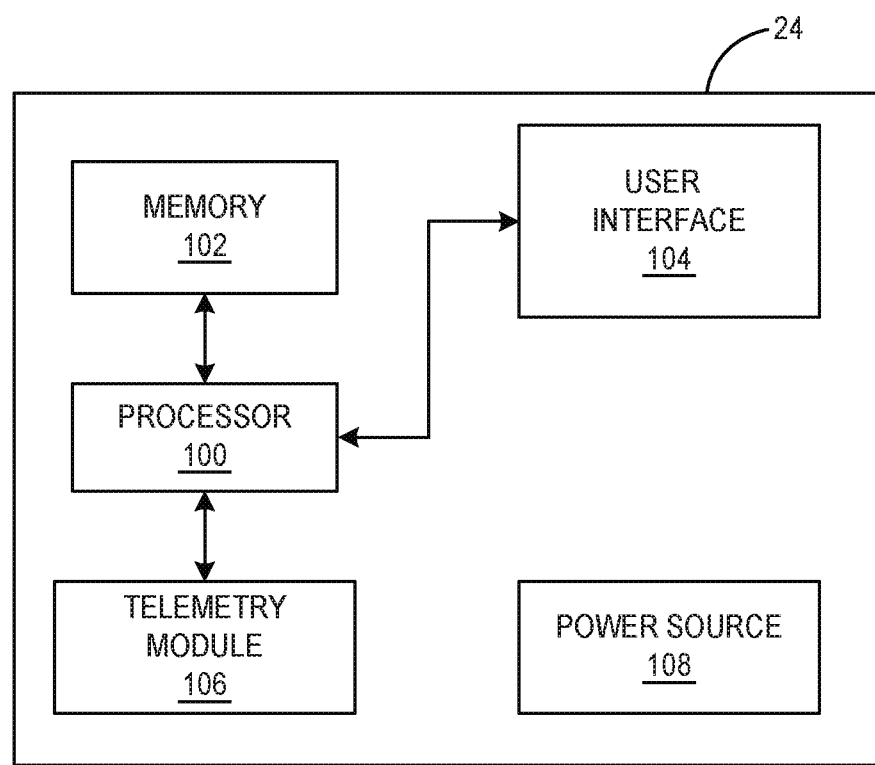
FIG. 4 is a functional block diagram illustrating an example configuration of an external programmer that facilitates user communication with the IMD.

FIG. 4 is a functional block diagram illustrating an example configuration of external programmer 24. As shown in FIG. 4, programmer 24 may include a processor 100, memory 102, user interface 104, telemetry module 106, and power source 108. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to configure the operational parameters of and retrieve data from IMD 16 (FIG. 1). The clinician may interact with programmer 24 via user interface 104, which may include display to present graphical user interface to a user, and a keypad or another mechanism for receiving input from a user. In addition, the user may receive an alert or notification from IMD 16 indicating the heart failure risk level and/or patient metrics via programmer 24. In other words, programmer 24 may receive diagnostic information from IMD 16.

Processor 100 can take the form one or more microprocessors, DSPs, ASICs, FPGAs, programmable logic circuitry, or the like, and the functions attributed to processor 100 herein may be embodied as hardware, firmware, software or any combination thereof. Memory 102 may store instructions that cause processor 100 to provide the functionality ascribed to programmer 24 herein, and information used by processor 100 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient.

Programmer 24 may communicate wirelessly with IMD 16, such as using RF communication or proximal inductive interaction. This wireless communication is possible through the use of telemetry module 106, which may be coupled to an internal antenna or an external antenna. An external antenna that is coupled to programmer 24 may correspond to the programming head that may be placed over heart 12, as described above with reference to FIG. 1. Telemetry module 106 may be similar to telemetry module 88 of IMD 16 (FIG. 4).

Telemetry module 106 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In this manner, telemetry module 106 may transmit an interrogation request to telemetry module 88 of IMD 16. Accordingly, telemetry module 106 may receive data (e.g. diagnostic information, real-time data related to absolute intrathoracic impedance that may be indicative of hypervolemia or hypovolemia, etc.) or diagnostic information selected by the request or based on already entered patient status to IMD 16. The data may include patient metric values or other detailed information from telemetry module 88 of IMD 16. The data may include an alert or notification of the heart failure risk level from telemetry module 88 of IMD 16. The alert may be automatically transmitted, or pushed, by IMD 16 when the heart failure risk level becomes critical. In addition, the alert may be a notification to a healthcare professional, e.g., a clinician or nurse, of the risk level and/or an instruction to patient 14 to seek medical treatment for the potential heart failure condition that may require re-hospitalization is left untreated. In response to receiving the alert, user interface 104 may present the alert to the healthcare professional regarding the risk level or present an instruction to patient 14 to seek medical treatment.

Either in response to heart failure data, e.g., the risk level or patient metrics, or requested heart failure information, user interface 104 may present the patient metrics and/or the heart failure risk level to the user. In some examples, user interface 104 may also highlight each of the patient metrics that have exceeded the respective one of the plurality of metric-specific thresholds. In this manner, the user may quickly review those patient metrics that have contributed to the identified heart failure risk level.

Upon receiving the alert via user interface 104, the user may also interact with user interface 104 to cancel the alert, forward the alert, retrieve data regarding the heart failure risk level (e.g., patient metric data), modify the metric-specific thresholds used to determine the risk level, or conduct any other action related to the treatment of patient 14. In some examples, the clinician may be able to review raw data to diagnose any other problems with patient 14 or monitor the efficacy of treatments given to patient 14. For example, the clinician may check if the intrathoracic impedance has increased after diuretic therapy or if the heart rate has decreased during atrial fibrillation in response to a rate controlling drug. User interface 104 may even suggest treatment along with the alert, e.g., certain drugs and doses, to minimize symptoms and tissue damage that could result from heart failure. User interface 104 may also allow the user to specify the type and timing of alerts based upon the severity or criticality of the heart failure risk level. In addition to the heart failure risk level, in other examples, user interface 104 may also provide the underlying patient metrics to allow the clinician to monitor therapy efficacy and remaining patient conditions.

In some examples, processor 100 of programmer 24 and/or one or more processors of one or more networked computers may perform all or a portion of the techniques described herein with respect to processor 80, metric detection module 92 and IMD 16. For example, processor 100 or a metric detection module 92 within programmer 24 may analyze patient metrics to detect those metrics exceeding thresholds and to generate the heart failure risk level.

Figure 5:
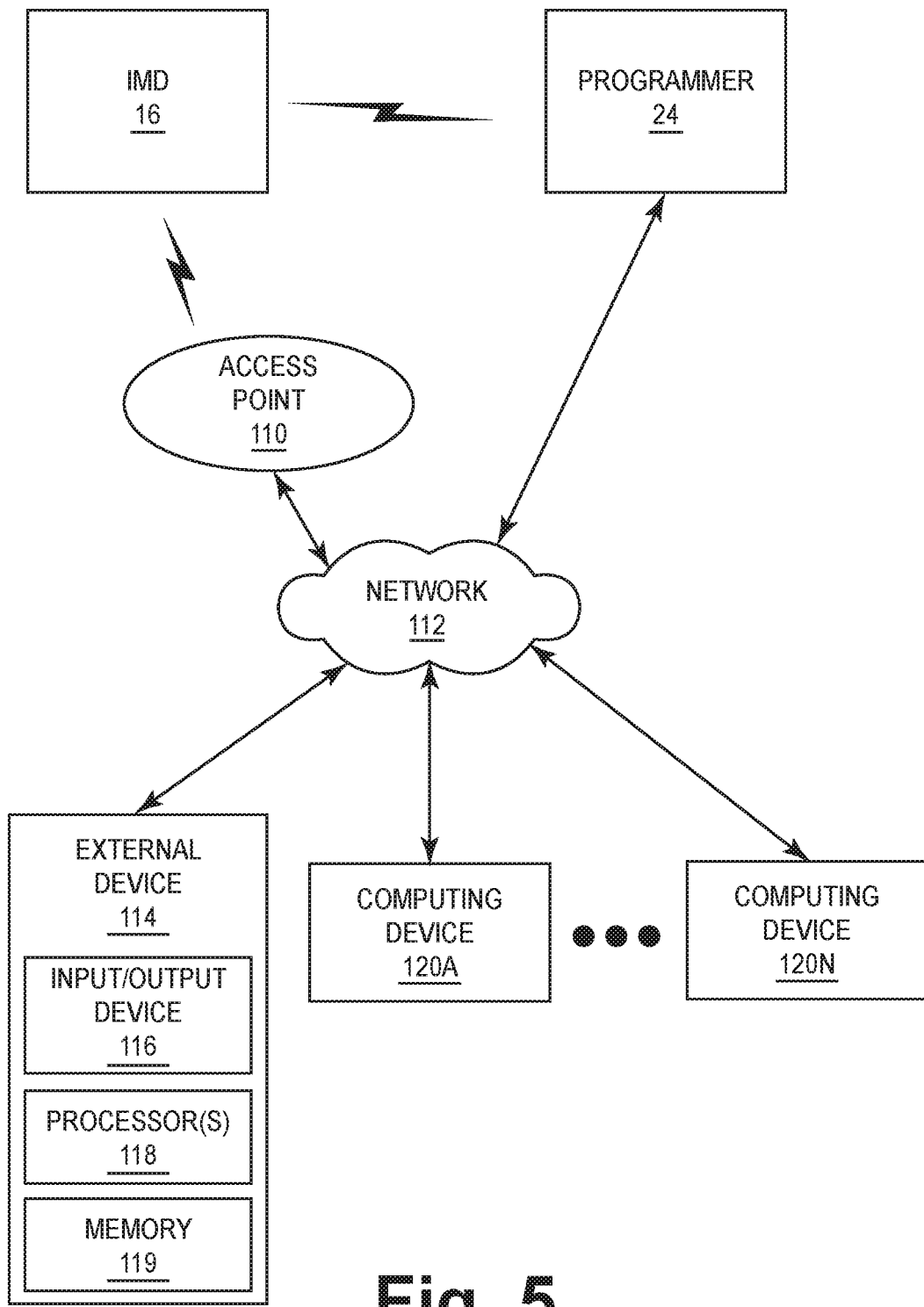
FIG. 5 is a block diagram illustrating an example computer system that includes an external device and one or more computing devices that are coupled to the IMD and programmer shown in FIG. 1 via a network.
Figure 6:
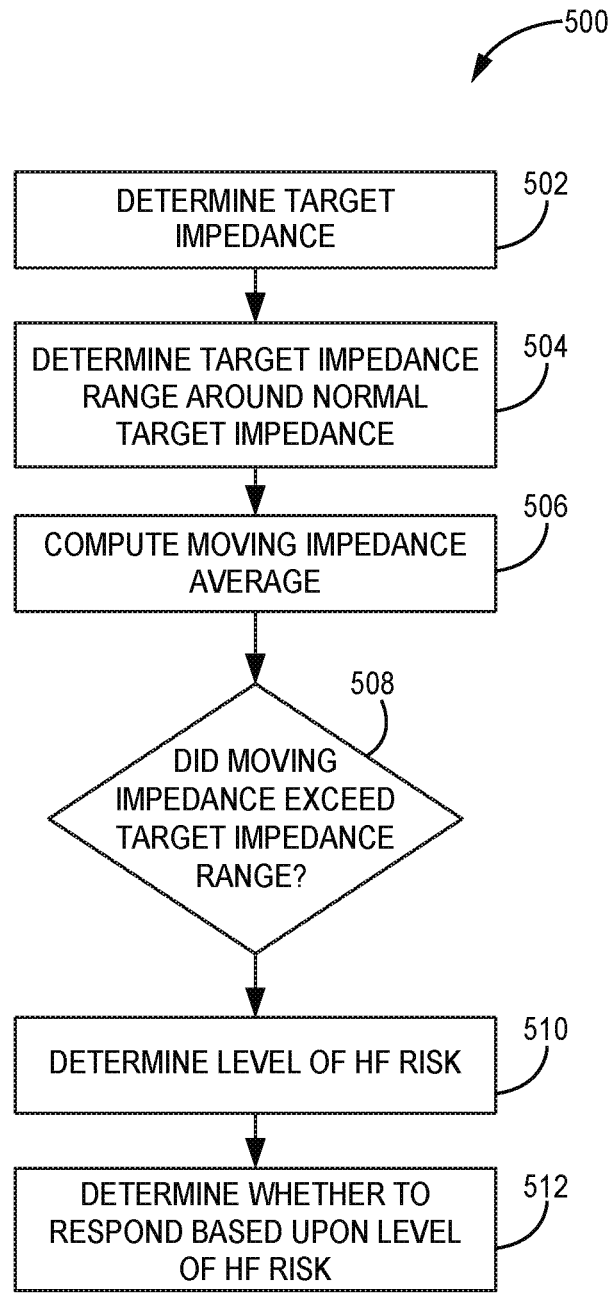
FIG. 6 depicts a flow diagram that predicts prospective risk of heart failure event for a patient.
Figure 7:
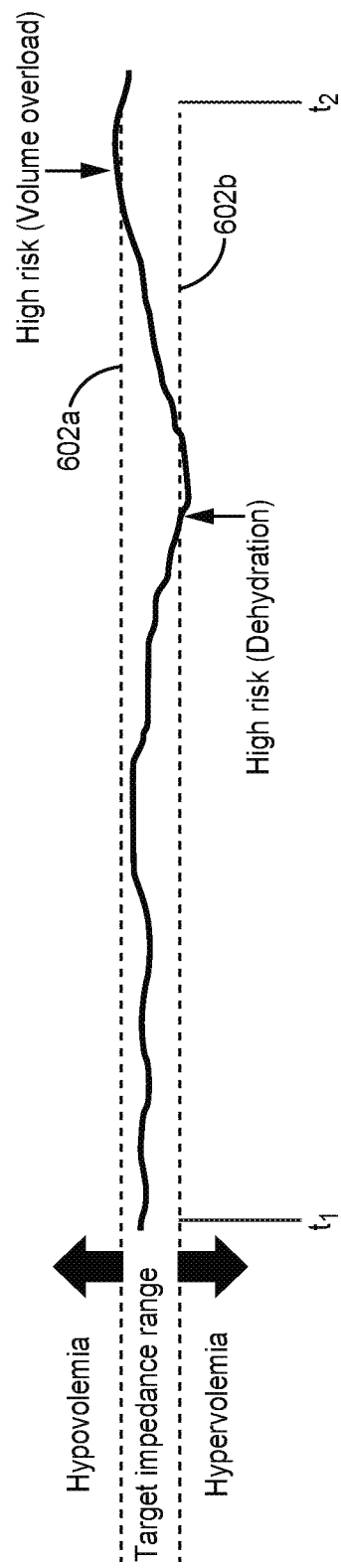
FIG. 7 graphically depicts an exemplary targeted impedance range that includes first and second ranges that serve as upper and lower boundaries extending vertically away from the normal impedance (or reference) with values between the upper and lower boundaries deemed within an acceptable impedance range for a patient.

FIG. 5 is a block diagram illustrating an example system that includes an external device 114 (e.g. server, etc.), and one or more computing devices 120A-120N, that are coupled to the IMD 16 and programmer 24 shown in FIG. 1 via a network 112. Network 112 may be generally used to transmit diagnostic information (e.g., a risk level) from a remote IMD 16 to another external computing device. However, network 112 may also be used to transmit diagnostic information from IMD 16 to an external computing device within the hospital so that a clinician or other healthcare professional may monitor patient 14. In this example, IMD 16 may use its telemetry module 88 to communicate with programmer 24 via a first wireless connection, and to communication with an access point 110 via a second wireless connection. In one or more embodiments, access point 110 may be an implantable device, such as LINQ™, which is configured to record date. An example of such a configuration may be seen with respect to U.S. patent application Ser. No. 15/133,354 filed on Apr. 20, 2016, and assigned to the assignee of the present invention, the disclosure of which is incorporated by reference in its entirety herein. The LINQ™ device, commercially available from Medtronic, can be implanted subcutaneously near the patient's heart. In the example of FIG. 5, access point 110, programmer 24, external device 114, and computing devices 120A-120N are interconnected, and able to communicate with each other, through network 112. In some cases, one or more of access point 110, programmer 24, external device 114, and computing devices 120A-120N may be coupled to network 112 through one or more wireless connections. IMD 16, programmer 24, external device 114, and computing devices 120A-120N may each comprise one or more processors, such as one or more microprocessors, DSPs, ASICs, FPGAs, programmable logic circuitry, or the like, that may perform various functions and operations, such as those described herein. Access point 110 may comprise a device (e.g. LINQ™) that connects to network 112 via any of a variety of connections, such as telephone dial-up, digital subscriber line (DSL), or cable modem connections. In other examples, access point 110 may be coupled to network 112 through different forms of connections, including wired or wireless connections. In some examples, access point 110 may be co-located with patient 14 and may comprise one or more programming units and/or computing devices (e.g., one or more monitoring units) that may perform various functions and operations described herein. For example, access point 110 may include a home-monitoring unit that is co-located with patient 14 and that may monitor the activity of IMD 16. In some examples, external device 114 or computing devices 120 may control or perform any of the various functions or operations described herein, e.g., generate a heart failure risk level based on the patient metric comparisons or create patient metrics from the raw metric data. External device 114 further includes input/output device 116, processor 118 and memory 119. Input/output device 116 includes input devices such as a keyboard, a mouse, voice input etc. and output device includes graphical user interfaces, printers and other suitable means. Processor 118 includes any suitable processor such as Intel Xeon Phi. Processor 118 is configured to set the start and end dates for each evaluation period. The evaluation period serves as an evaluation window that encompasses data, acquired from each patient, that are within the boundaries (i.e. start and end times). Processor 118 is also configured to perform a variety of calculations. For example, processor 118 calculates risk of HF event (HFH risk) for each evaluation period. In one or more embodiments, weighting factors are applied to two or more evaluations periods to determine the Frisk.

Memory 119 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Memory 119 stores data. Exemplary data stored in memory 119 includes heart failure patient data, heart failure prospective risk data etc. Evaluation period start and end times are also stored in memory. Heart failure patient data includes data observations (e.g. data sensed from sensors that cross a threshold). Additionally, evaluation period data is also stored in memory 119. For example, the start and end dates of the evaluation period data is stored in memory 119.

In some cases, external device 114 may be configured to provide a secure storage site for archival of diagnostic information (e.g., patient metric data and/or heart failure risk levels) that has been collected and generated from IMD 16 and/or programmer 24. Network 112 may comprise a local area network, wide area network, or global network, such as the Internet. In some cases, programmer 24 or external device 114 may assemble the diagnostic data, heart failure data, prospective heart failure risk data or other suitable data in web pages or other documents for viewing by and trained professionals, such as clinicians, via viewing terminals associated with computing devices 120. The system of FIG. 5 may be implemented, in some aspects, with general network technology and functionality similar to that provided by the Medtronic CareLink® Network developed by Medtronic, Inc., of Minneapolis, Minn.

In the manner of FIG. 5, computing device 120A or programmer 24, for example, may be remote computing devices that receive and present diagnostic information transmitted from IMDs of multiple patients so that a clinician may prioritize the patients needing treatment immediately. In other words, the clinician may triage patients by analyzing the HFH levels of multiple patients. The computing device may use its communication module to receive the diagnostic information (e.g., heart failure data) transmitted from multiple IMDs via network 112.

Diagnostic metrics, typically indicative of worsening heart failure, mortality risk and/or hospitalization risk, include an (1) impedance trend index (also referred to as OPTIVOL® commercially available in IMDs from Medtronic Inc., located in MN), (2) intrathoracic impedance, (3) atrial tachycardia/atrial fibrillation (AT/AF) burden, (4) mean ventricular rate during AT/AF, (5) patient activity, (6) Ventricular (V) rate, (7) day and night heart rate, (8) percent CRT pacing, and/or (9) number of shocks. The OPTIVOL® index is an indicator of the amount of fluid congestion experienced by the patient. The OPTIVOL® index is the difference between an impedance measured during real time using IMD 16 and a reference impedance, that can be continuously updated, established by the IMD 16 or during another visit to the physician. OPTIVOL® is described in greater detail with respect to U.S. patent Ser. No. 10/727,008 filed on Dec. 3, 2003 issued as U.S. Pat. No. 7,986,994, and assigned to the assignee of the present invention, the disclosure of which is incorporated by reference in its entirety herein.

FIGS. 6-14 are directed to using absolute intrathoracic impedance based scheme to stratify patients for risk of HFH. Method 500, depicted in FIG. 6 and implemented by the system shown in FIG. 5, determines whether to generate some type of response to a measured intrathoracic electrical impedance (Z) relative to a moving average impedance for a patient. An example of the manner in which to measure intrathoracic electrical impedance is described in U.S. Pat. No. 7,986,994 issued Jul. 26, 2011, entitled METHOD AND APPARATUS FOR DETECTING CHANGE IN INTRATHORACIC ELECTRICAL IMPEDANCE and assigned to the assignee of the present invention, the disclosure of which is incorporated by reference in its entirety herein.

To measure intrathoracic electrical impedance, an implantable medical device 16 (e.g. ICD, pacemaker (IPG) etc.) is implanted on the left side or on the right side, and can have a lead extending through the right atrium (RA) and into the right ventricle (RV) of the heart. While the disclosure describes an implantable medical device such as a pacemaker and lead combination are implanted into a living body, alternative types of implantable medical devices may also be used, including for example, leadless implantable medical devices, defibrillators, drug infusion devices, spinal cord stimulators or any other implantable device having the minimum external number of electrodes and being provided with an impedance stimulation and measurement circuit. An example of a leadless implantable medical devices is described in U.S. patent application Ser. No. 13/096,881 filed on Apr. 28, 2011, entitled IMPLANTABLE MEDICAL DEVICE FIXATION and assigned to the assignee of the present invention, the disclosure of which is incorporated by reference in its entirety herein.

Method 500 begins at block 502 in which a normal impedance value for a patient is determined. While the normal impedance for the patient may not be within an optimal range for a healthy person, the normal impedance is considered typical for the patient and becomes the target level that is desired to be maintained since patients typically experience deteriorating health as time progresses. The normal impedance serves as a reference or baseline level for that patient from which subsequently acquired raw impedance data is compared. For example, raw impedance can be acquired from the electrodes (e.g. RV coil to Can) and compared to the reference impedance.

One exemplary manner of determining a normal impedance value occurs during a pre-determined time period (e.g. intrathoracic electrical impedance repeatedly tested over a 30 day window, 14 day window etc.) that has a certain prescribed amount of time (e.g. two weeks, three weeks, 4 weeks, 5 weeks, 6 weeks, etc.) away from a heart failure event. Additionally or alternatively, a normal impedance value can be determined by verifying that device parameters are in, or trending in, a normal or targeted range over a certain period of time. Device parameters that are indicative of a trend in a normal range include that the patient is not presently exhibiting atrial fibrillation (AF), a NHR<85 bpm, physical activity of the patient is greater than 1 hour per day, 60 milliseconds (ms)<HRV<150 ms, and if the patient is experiencing chronic AF the HR<90 bpm.

At block 504, a targeted impedance range is established for a particular patient to help determine whether the patient is within an acceptable impedance range. The targeted impedance range includes first and second ranges 602a,b (also referred to as first and second ranges) that serve as upper and lower boundaries extending vertically away from the normal impedance (or reference) with values therebetween that are deemed within an acceptable range for the patient. Targeted impedance range data is created for the specific patient using data from the patient and/or a general population of patient data. Targeted impedance range is based upon data obtained from the patient at a time in which the patient is relatively healthy and not presently experiencing a HF event. For example, FIGS. 1A-11B present exemplary impedance values for a patient from the time the IMD 16 is implanted until a HFH is experienced by the patient as shown in FIG. 11B. A baseline mean impedance was calculated over a thirty day period. A blanking period (e.g. 14 days) is implemented immediately before determining the baseline mean impedance and immediately after a HF event to ensure that the baseline impedance value is representative of a patient's typical physical condition. A blanking period indicates that the impedance values are either not acquired from electrodes for the purpose of determining the target impedance range or the mean impedance value is not calculated using data acquired during the blanking period.

Figure 10:
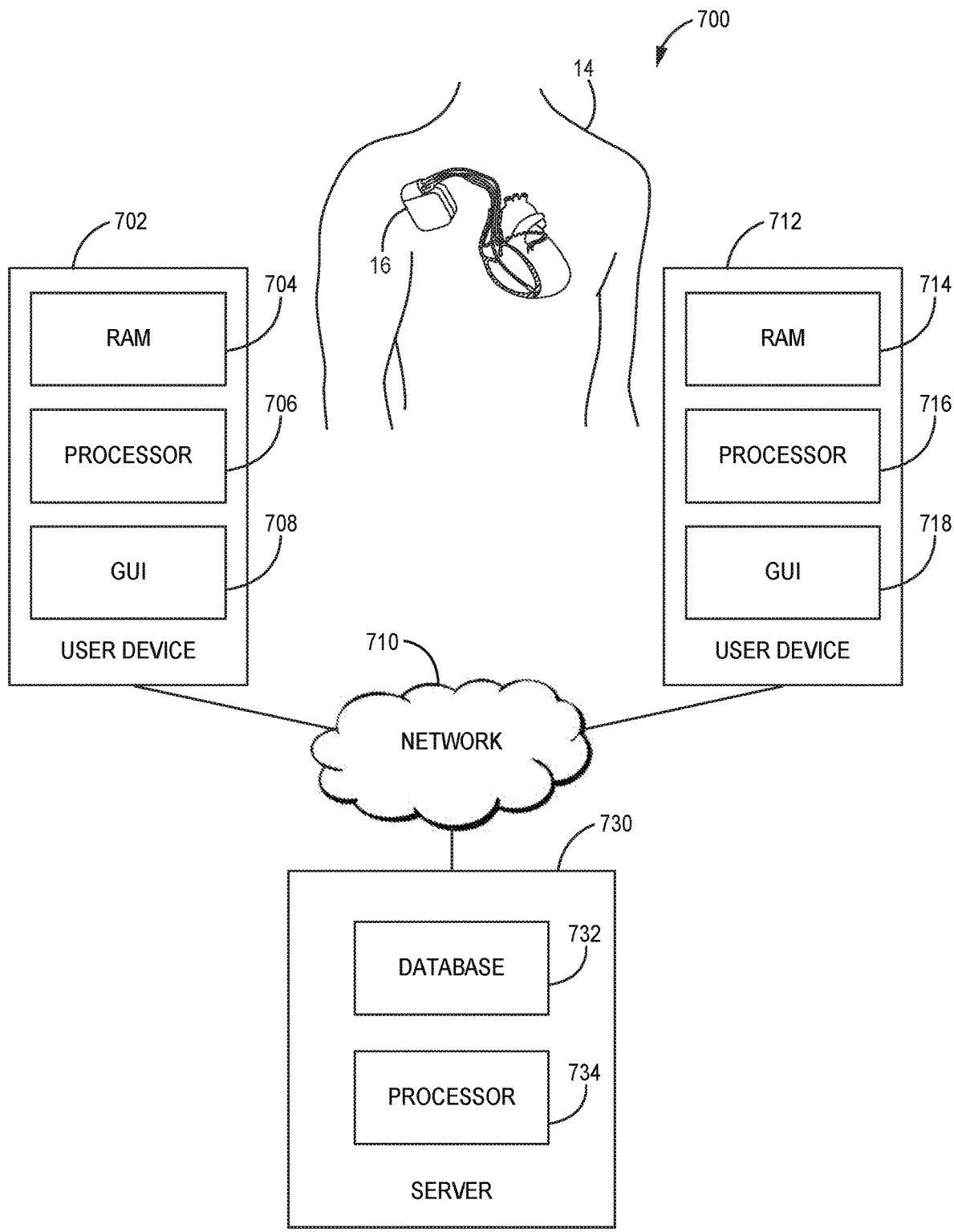
FIG. 10 is a block diagram illustrating an example computer system that includes an external device and one or more computing devices that are coupled to the IMD and programmer shown in FIG. 1 via a network.
Figure 11:
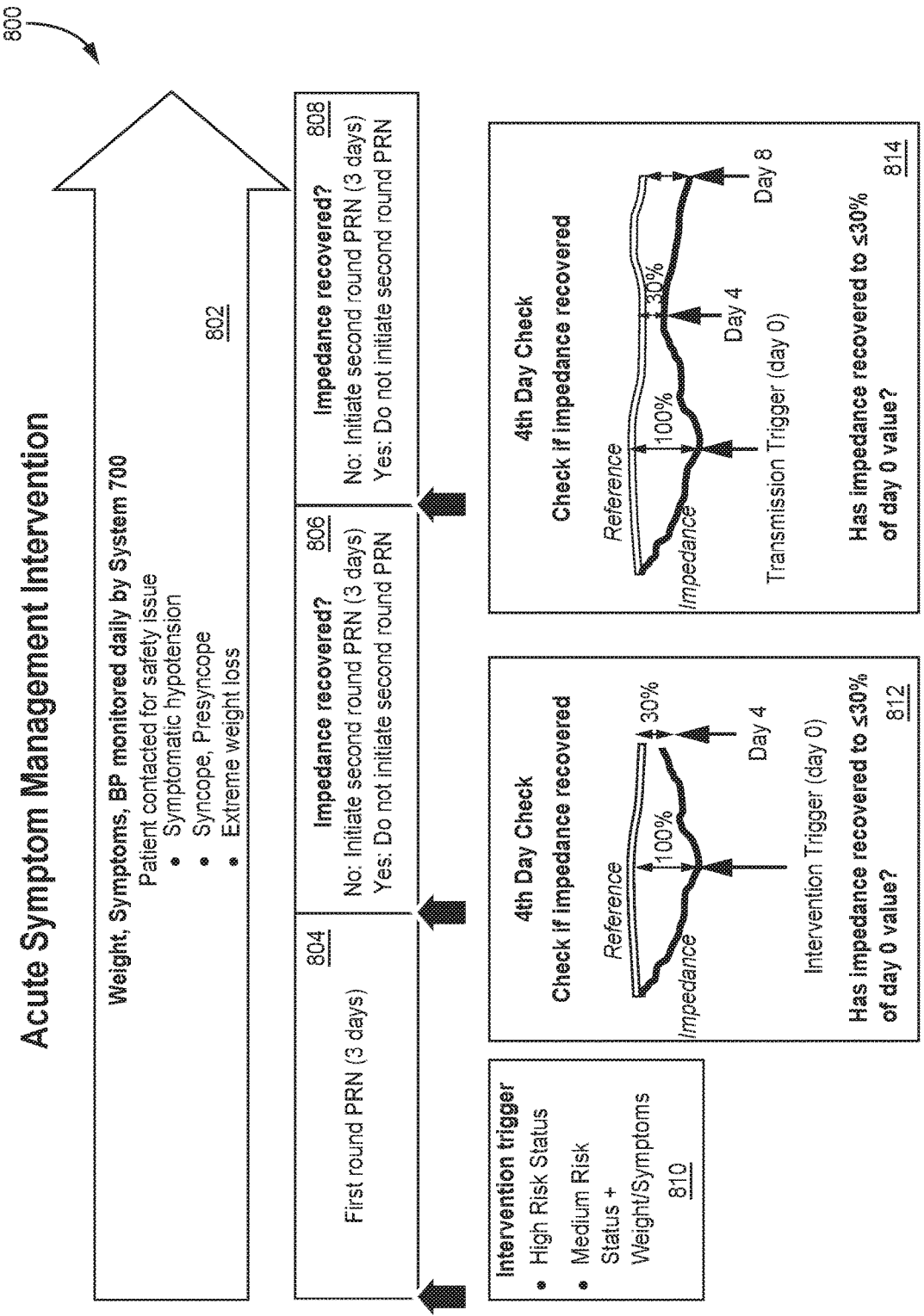
FIG. 11 is a flow diagram of an exemplary symptom management intervention system that can cause one or more adjustments to therapy that is being delivered to a patient.

An exemplary normal impedance range for a HF patient, defined by a first and second range 602a,b, is depicted in FIG. 10. The first and second range 602a,b, extend horizontally from time t1 to t2. The first and second range 602a,b, serve as upper and lower boundaries for the targeted impedance range for a particular patient. The first range 602a serves as a higher value boundary of intrathoracic electrical impedance. Too high intrathoracic electrical impedance values (i.e. exceeding the first range 602a), acquired after the targeted intrathoracic electrical impedance range has been developed, indicates that the patient is experiencing hypovolemia. Hypovolemia means the patient is at risk of fluid volume overload. In contrast, the second range 602b serves as a boundary for lower values of intrathoracic electrical impedance. Too low a value of intrathoracic electrical impedance (i.e. intrathoracic electrical impedance values lower than the second range 602b) is indicative of hypovolemia. Symptoms of hypervolemia include swollen legs, swollen arms and/or fluid in and abdomen. Excess fluid in the blood can enter air spaces in the lungs which is referred to as pulmonary edema.

In one or more embodiments, the first and second ranges 602a,b can be symmetrical to each other. Symmetrical ranges means that the first and second ranges 602a,b are equidistant away from the target impedance range (also referred to as the reference intrathoracic electrical impedance). For example, the first range 602a extends +7% away from the target impedance range (also referred to as the reference intrathoracic electrical impedance) while the second range 602b extends -7% away from the target impedance range. In one or more other embodiments, the first and second ranges 602a,b can be asymmetrical to each other such that one of the first and second ranges 602a,b are closer to the target impedance range than the other range. For example, the first range 602a can extend +4% while the second range 602b can extend -7% away from the target impedance range. Asymmetrical first and second ranges 602a,b may be preferred over symmetrical first and second ranges 602a,b as to estimating the risk of hypovolemia, hypervolemia, or HFH.

Employing the first and second ranges 602a,b provides a bright-line test for determining elevated risk of a HF event such that real-time impedance data that is outside the normal or targeted range (e.g. average impedance data is either too high or too low) signifies elevated risk. This absolute impedance based scheme is referred to as OPTIZ™. In particular, OPTIZ™ is the complete scheme with establishment of normal impedance and upper and lower ranges around it. According to one or more embodiments, cut-off ranges can be up to +10% of the baseline mean impedance on the hypovolemia diagnosis and up to -10% on the hypervolemia diagnosis. Performance of the scheme to predict a HF event was evaluated using data acquired from PARTNERS-HF trial and compared against data obtained from patients having implantable medical devices capable of measuring intrathoracic electrical impedance (i.e. OPTIVOL®). Table 1, presented below, compares the performance in predicting HF event (e.g. HFH) (i.e. 7% range or band and two consecutive out-of-range values were used to flag high risk). Sensitivity is the probability that an impedance test is indicative of HFH. Positive predictive value is the probability in which subjects with a positive screening test truly have the disease. Even a single point or few points may be out of range can signify that impedance has been trending in the wrong direction for some time. Therefore, even one or a few points outside of the normal impedance range (e.g. 7%) can be predictive of HF worsening.

TABLE 1

| Impedance monitoring results indicative of HF event (HFH)Parameter | Sensitivity | Positive Predictive Value |
| --- | --- | --- |
| OptiVol ™ | 73.7% | 5.4% |
| OptiZ ™ | 72.1% | 5.9% |

At block 506, a moving impedance average is computed over a pre-specified time period for a patient. Exemplary time periods in which the moving impedance average is computed include 30 days or less, 25 days or less, 20 days or less, 15 days or less, 10 days or less, 9 days or less, 8 days or less, 7 days or less, 6 days or less, 5 days or less, 4 days or less, 3 days or less, 2 days or less, 24 hours. Preferably, the moving impedance average is computed over a 7 day period. Moving impedance average is a succession of impedance averages derived from successive segments of a series of impedance values. The successive segments are typically of constant size and overlapping. However, successive segments can be established as varied sizes when impedance values exhibit a substantial increases or decreases in a short period of time.

Figure 9A:
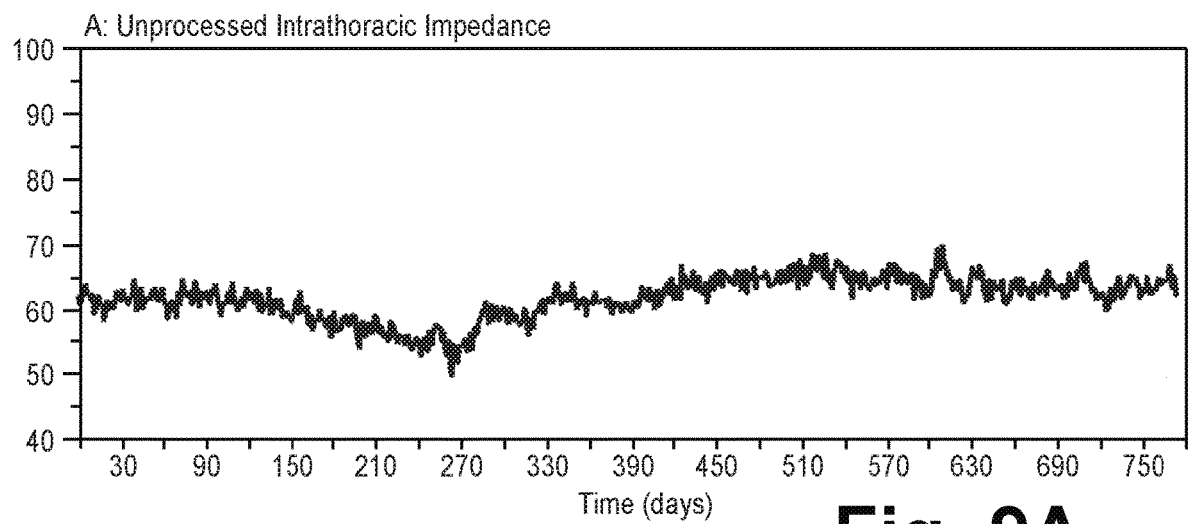
FIG. 9A graphically depicts unprocessed raw intrathoracic values to impedance values.
Figure 9B:
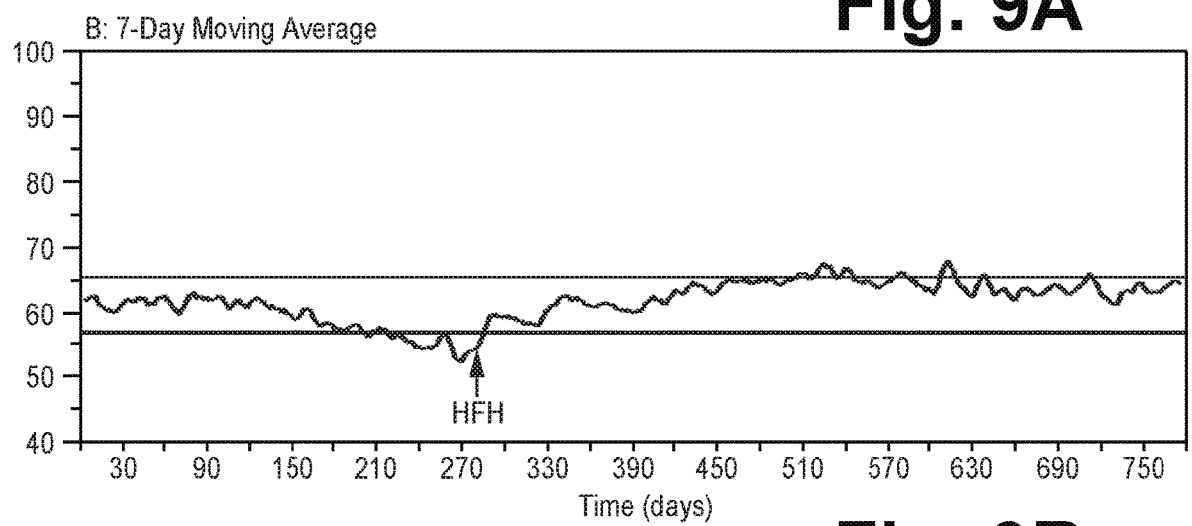
FIG. 9B graphically depicts impedance values with upper and lower ranges over a pre-specified moving day average for a patient.

At block 508, a determination is made as to whether the moving average of impedance exceeds the targeted impedance range. This step involves comparing the moving average of impedance value to the upper and/or lower boundaries established at block 504. FIGS. 9A-9B depict raw unprocessed intrathoracic impedance to a moving 7-day average of the intrathoracic impedance. As shown, some of the impedance values exceed upper and lower boundaries for the targeted impedance. For example, the moving average of impedance value is within an acceptable target range from days 0 to 200 days, 290-490 days. The moving average of impedance value exceeds the lower boundary at about 200 to about 290 days. The moving average intermittently exceeds the upper range from about 500 to about 700 days. A decrease in impedance and excursion outside the lower bound was followed by a HFH which occurs at about day 280. Thus, the impedance drop outside the boundary can serve as an early warning to perform HF intervention and avert HF event (e.g. HFH).

In addition to the different band widths, the numbers of days outside of the range was also considered (1 day and 2, 3, or 4 consecutive days). Positive predictive value (PPV) was evaluated for each impedance trigger that did not have a previous trigger within 30 days. A trigger was considered positive if HFH occurred within 30 days. Sensitivity was evaluated for each HFH that had a 7-day moving average impedance value available for the 30 days prior to the HFH. Presently, it is preferred to have a 7 day moving average for impedance value.

Data supporting the 7 day moving average for impedance is presented in Tables 2 and 3. Table 2 shows demographics of 106 patients included in the retrospective analysis. All patients had a ICD or a CRT-D device. The majority of patients (~92%) were classified as NYHA II or III. FIG. 9A shows representative traces of an unprocessed impedance signal and FIG. 9B shows a 7-day moving average impedance signal. Also shown in FIG. 9B is a 7% range around the moving average impedance signal.

Table 3 shows the sensitivity and PPV of predicting a HF hospitalization for a 7-day moving average and various combinations of impedance ranges and consecutive out-of-zone days to trigger a hospitalization flag. For a ±6% range, the sensitivity of HFH detection was 80% and positive predictive value (PPV) was 5.1%. PPV increased and sensitivity decreased gradually when 2, 3, or 4 "Z" (impedance) measurements outside Z range were required for the trigger. Additionally, selecting a larger range tended to increase PPV and decrease sensitivity. OPTIVOL® had a sensitivity of 75% and PPV of 6.6%.

TABLE 2

Demographics of 106 patients included in the data analysis

| | |
| --- | --- |
| Male | 80 (75.5%) |
| Mean Age | 69.6 ± 11.1 |
| NYHA | |
| I | 9 (8.5%) |
| II | 65 (61.3%) |
| III | 32 (30.2%) |
| Device type: ICD, | 12 (11.3%), |
| CRT-D | 94 (88.7%) |
| Ischemic Cardiomyopathy | 71 (67.0%) |
| Nonischemic Cardiomyopathy | 36 (34.0%) |
| Coronary Artery Disease | 76 (71.7%) |
| Diabetes | 43 (40.6%) |
| History of Hypertension | 73 (68.9%) |

Out-of-range Z values can be used to predict HFH with positive predictive value (PPV) and sensitivity that is comparable to OptiVol.

TABLE 3 presents PPV and sensitivity in predicting hospitalization for various combinations of impedance zone and consecutive out-of-zone criterion.

| | PPV | Sensitivity |
| --- | --- | --- |
| 7-day Moving Average | | |
| ±6% Band | 36/709 (5.1%) | 32/40 (80.0%) |
| ±6% Band-2 days | 34/658 (5.2%) | 32/40 (80.0%) |
| ±6% Band-3 days | 34/614 (5.5%) | 31/40 (77.5%) |
| ±6% Band-4 days | 32/566 (5.7%) | 28/40 (70.0%) |
| ±7% Band | 34/560 (6.1%) | 29/40 (72.5%) |
| ±7% Band-2 days | 32/515 (6.2%) | 28/40 (70.0%) |
| ±7% Band-3 days | 31/486 (6.4%) | 27/40 (67.5%) |
| ±7% Band-4 days | 31/457 (6.8%) | 25/40 (62.5%) |
| ±8% Band | 33/444 (7.4%) | 27/40 (67.5%) |

TABLE 3-continued presents PPV and sensitivity in predicting hospitalization for various combinations of impedance zone and consecutive out-of-zone criterion.

|  | PPV | Sensitivity |
|---|---|---|
| ±8% Band-2 days | 30/406 (7.4%) | 25/40 (62.5%) |
| ±8% Band-3 days | 27/377 (7.2%) | 23/40 (57.5%) |
| ±8% Band-4 days | 29/353 (8.2%) | 23/40 (57.5%) |
| OPTIVOL ® >60 | 32/485 (6.6%) | 30/40 (75.0%) |

Figure 12:
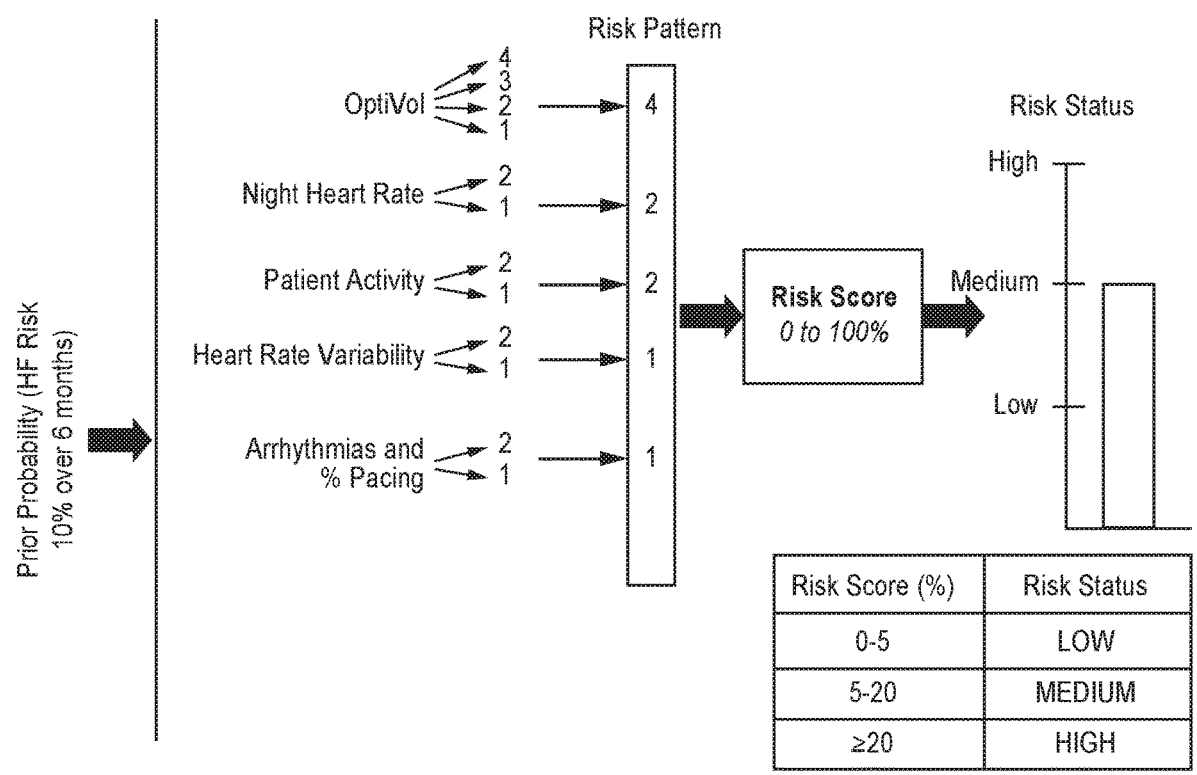
FIG. 12 is a block diagram of integrated diagnostics related to risk status.

At block 510, the level of HF event risk (e.g. HFH risk) is determined based upon whether the moving average of impedance is outside of the targeted impedance range. Skilled artisans understand that the risk of a HF event (e.g. HFH) is increased when the moving average of impedance is outside of the targeted impedance range. In one or more other embodiments, an integrated diagnostics approach can be implemented in which various parameters (e.g. OPTIVOL®, night heart rate, patient activity, heart rate variability, arrhythmias and percent pacing) are associated with a particular risk pattern. Based upon the parameter that exceeds a threshold, the patient's risk score is calculated and then classified as high, medium or low risk. Exemplary medium and high risk stratification are shown and described in US20120109243, entitled HEART FAILURE MONITORING AND NOTIFICATION and assigned to the assignee of the present invention, the disclosure of which is incorporated by reference in its entirety herein. FIG. 12 depicts integrated diagnostics relative to the risk of heart failure. The risk stratification process relies on a baseline probability of HFH of 10% over six months for a group of patients. The device variables were assigned discrete states such that the higher state was associated with a greater likelihood of a heart failure event (e.g. OPTIVOL ranked a 4 for extreme impedance values) while a lower state (e.g. impedance within a relatively normal range is assigned a value of "1" while the remaining parameters (e.g. night heart rate, patient activity, heart rate variability, arryhythmias and percent pacing are ranked "1" or "2") was associated with a lower likelihood of a heart failure event. The variables states were then used to generate a risk pattern signatures which were then used to generate a risk score using a Bayesian Belief Network model. The score ranged from 0-100%. Numerical scores serve as cut-offs to stratify or classify a patient evaluation into low, medium or high risk status. The numerical risk was modulated around the baseline prior probability of 10%.

Depending upon the HFH risk, a variety of responses may occur at block 512. For example, the health care worker (e.g. physician, nurse etc.) may be automatically notified through a communication (e.g. electronic health alert such as a CareAlert, an intrathoracic electrical impedance transmission (i.e. OPTIVOL® etc.) and/or other like alerts) which may prompt them to make appropriate therapeutic intervention (e.g. a medication change). In one or more embodiments, therapy delivered by the IMD 16 can be adjusted. In one or more other embodiments, drug delivery to the patient may be implemented and/or adjusted, as shown and described relative to FIG. 14.

A variety of health care systems can be used to implement any one of the responses. For example, FIG. 10, a health care system 700 is depicted that is configured to automatically intervene to address symptoms experienced by a patient. The health care system 700 includes a server 730, user devices 702, 712 associated with the patient and physician respectively and network 710. User devices 702, 712 can comprise a desktop computer, laptop computer, a personal digital assistant (e.g. cell phone, iPad, or the like). User device 702 can electronically and wirelessly acquire data from IMD16 is electronically connected to patient data through network 710. Exemplary network 710 includes Medtronic CareLink® Network developed by Medtronic, Inc., of Minneapolis, Minn., or some other network linking patient 14 to a clinician. Patient data can be periodically and/or automatically uploaded from the patient's devices (IMD 16 and/or user device 702) through the network 710 to server 730, which is accessible by a clinician. Software updates and/or or storing of data (e.g. updated thresholds, and/or when to switch a response to a patient's symptoms, acute symptoms etc.) onto IMD 16 can be transmitted from a server such as server 730. Acute symptoms include shortness of breath, jugular vein distension, peripheral edema, and orthopnea (i.e. difficulty to lie flat on back). Acute symptoms are associated with the fact that patient has accumulated excess fluid. Some excess fluid may have crossed into the lung (e.g. pulmonary congestion). Server 730, IMD 15, and/or user device 702, 712, and/or the programmer can each determine whether patient parameters are changing over time.

Whether a patient begins to experience or is experiencing acute symptoms is based upon a variety of parameters that can change over time. Exemplary parameters 802 capable of changing over time includes the patient's weight (i.e. extreme weight loss), hypotension, syncope, pre-syncope, all of which can be uploaded to the system 700 on a periodic basis (e.g. daily basis) from the patient's computer or user device 702.

FIG. 11 depicts an exemplary acute symptom management intervention process 800 that is automatically implemented through system 700 or the computer system depicted in FIG. 5. Acute symptom management intervention process 800 comprises parameters 802, set of increased treatments 804, 806, 808, set of intervention triggers for one or more treatments 804, 806, 808, and periodic impedance checks 812, 814.

Intervention trigger 810 causes some response from system 700. Intervention trigger 810 indicates that after patient monitoring of certain parameters (e.g. monitoring for impedance etc.) the patient is considered to exhibit high risk status or medium risk status in addition to weight issues and/or other symptoms.

The first exemplary treatment 804 can be introduced to a patient over a prescribed amount of time utilizing a preauthorized prescription, if necessary. For example, after the thoracic impedance level is detected at a pre-specified level, a drug at a certain dosage (e.g. pro re nata (PRN) etc.) may be acquired by a patient for a certain amount of time (e.g. three days, etc.) provided a physician has preauthorized the prescription. After the prescribed amount of time, the impedance is again checked to determine whether improvement in the intrathoracic electrical impedance can be determined in response to the administered drug. If the impedance level acquired from the patient has adequately improved (e.g. within 30 percent of the baseline thoracic impedance), delivery of the drug may be suspended, maintained at its present level or decreased. The patient's physician may decide dosages depending upon the condition of the patient. The physician's decision on dosages may occur many months before the patient's condition has changed.

In alternative embodiments, the physician can be notified on his personal digital assistant (e.g. cell phone) of a needed adjustment to the patient's therapy. In this embodiment, the physician can either approve of the therapy from the system or modify the therapy.

If the thoracic impedance level acquired from the patient has not adequately improved after a prescribed amount of time, delivery of the drug may be increased in dosage at block 806 or maintained at its present level in addition to administering another treatment.

If the thoracic impedance level is still inadequate, delivery of the drug may be again increased in dosage at block 808, maintained at its present level in addition to administering another treatment. If the thoracic impedance level is adequate, delivery of the drug may be ceased at block 808, maintained at its present level, or adjusted (i.e. decreased).

Figure 13:
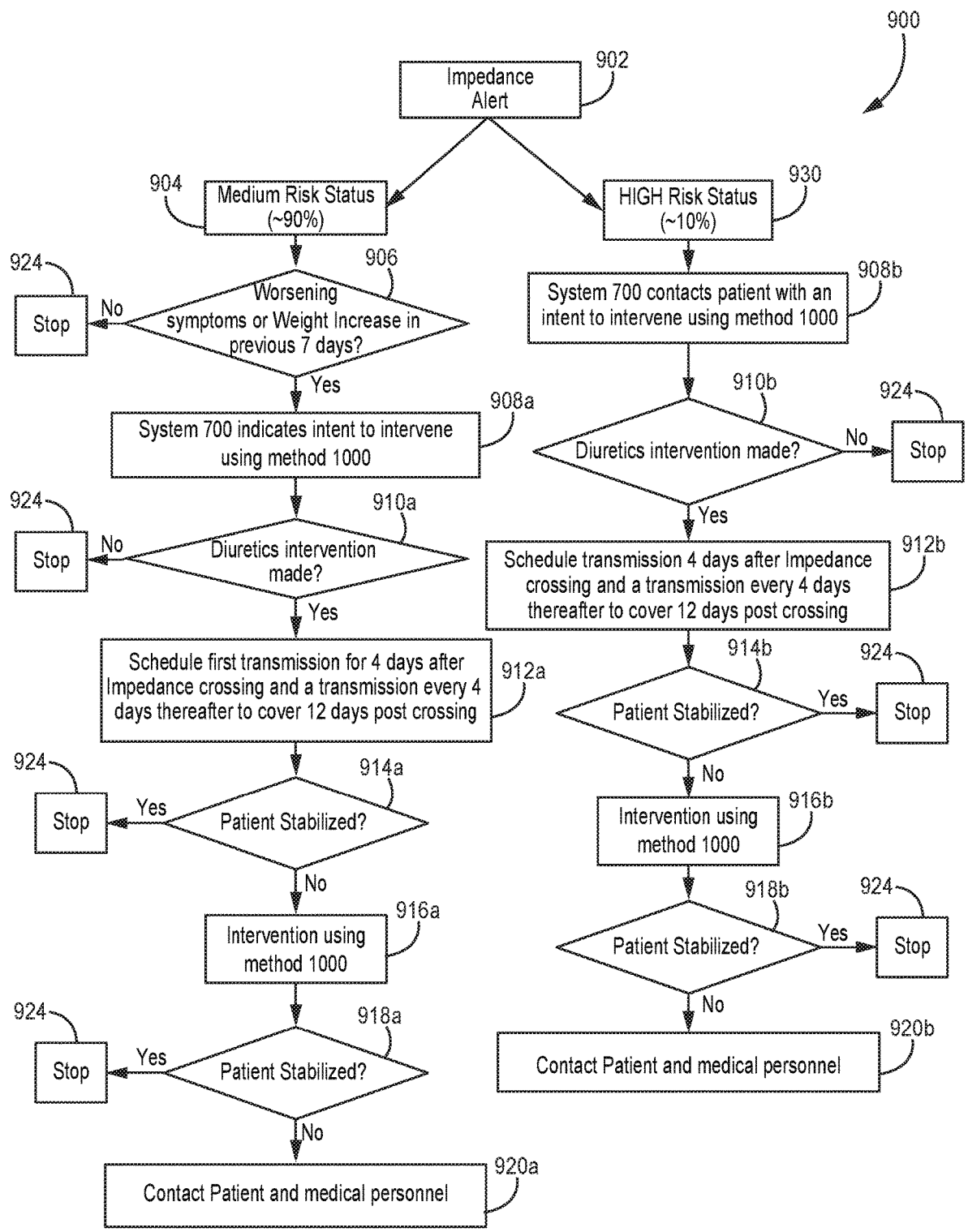
FIG. 13 is a block diagram in which a patient and/or health care worker is notified in response to a determination of the patient status.
Figure 14:
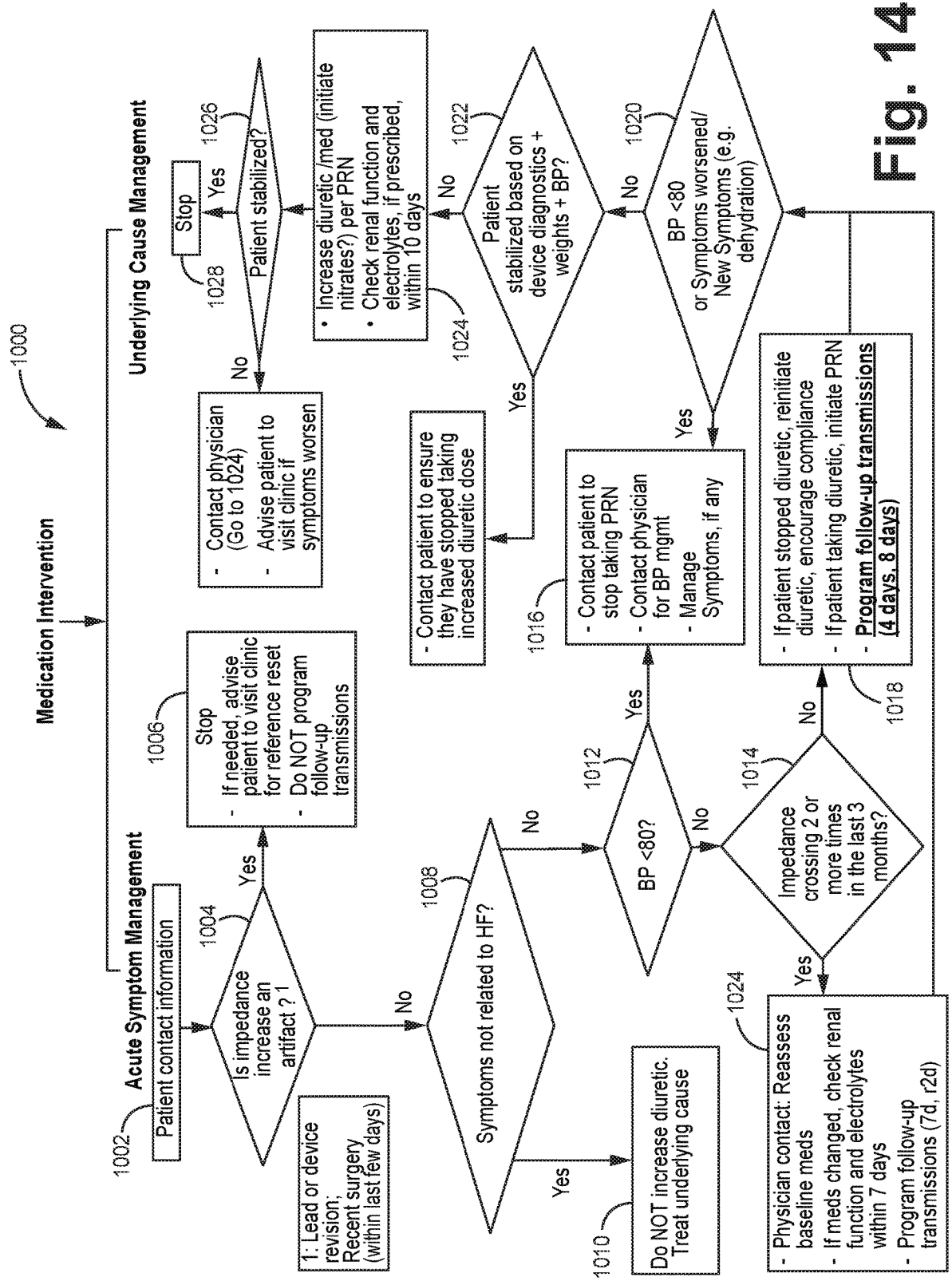
FIG. 14 is a block diagram in which therapy is initiated or adjusted in response to data detected and transmitted to a healthcare system.

FIG. 13 depicts a process 900 that can intervene with the therapy delivered to HF patients. Exemplary medium and high risk stratification are shown and described in US20120109243, entitled HEART FAILURE MONITORING AND NOTIFICATION and assigned to the assignee of the present invention, the disclosure of which is incorporated by reference in its entirety herein. Patients' deemed to possess medium risk status (~90% of the HF patients) undergo the same or similar intervention process (blocks 908a,b-920a,b) as the high risk status patients (~10% of the HF patients) except the medium risk status patients include the additional determination step of block 906, which is described below.

Process 900 begins at block 902 in which impedance monitoring has been occurring. After monitoring impedance in which the target impedance range for the patient has been exceeded, an alert may be automatically generated and sent to medical personnel, the patient, or both. An exemplary impedance alert can comprise an OPTIVOL® alert from the Medtronic CareLink® Network.

At block 906, a determination is made as to whether a patient is experiencing worsening symptoms or weight increase over a previous time period (e.g. 7 days). If the symptoms have not worsened over the prescribed time, the NO path from block 906 continues to block 924. In contrast, if the symptoms worsen over the prescribed time or weight is increased, the YES path continues to block 908a.

At block 908a, system 700 automatically contacts the patient, the medical personnel (e.g. physician etc.), or both with an alert of the worsening condition and/or a notification as to an intent to change of therapy delivered to the patient. After notification, the medical personnel has the option to cancel the modification to the therapy, confirm modification to therapy or merely allow the therapy modification to occur without confirmation.

At block 910a, a determination is made as to whether therapy intervention should be made as to administration of diuretics to the patient. Diuretics assist a patient in eliminating fluid (e.g. water) from the blood. If no intervention is required, the NO path from block 910a continues to block 924 which stops intervention operations as to deciding whether to adjust diuretics for the patient.

At block 912a, a transmission can be periodically scheduled a certain time period (e.g. every 4 days up to 12 days etc.) after an impedance boundary has been exceeded. At block 914a, a determination is made as to whether a patient is stable. Determining whether a patient is stable depend upon the patient's vital signs. If the patient is stabilized, the intervention operation is stopped at block 924. Recovery and/or stabilization criterion is based on impedance. If the impedance has recovered by 30% (or other threshold, which can be programmable and patient specific), next round of medication up titration (i.e. PRN) is not provided. Otherwise, the next PRN is initiated, If the patient is not stabilized, then an intervention operation occurs at block 916a. The intervention operation applicable to block 916a is selected from flow diagram 1000, which is described below.

After a certain time period has expired, at block 918a, a determination is made as to whether a patient is stabilized such that further intervention is unnecessary. If the patient is stabilized, the intervention operation is stopped at block 924. If the patient is not stabilized, then an intervention operation occurs at block at block 920a such that the medical personnel and/or the patient are contacted to schedule a visit the physician.

After intervention has been determined to be warranted from process 900, a medication intervention may be implemented according to method 1000. Method 1000 begins at block 1002 which requires the patient's contact information such as phone number, email address etc. to be electronically stored into memory of the system. According to method 900, the patient, periodically monitored for impedance, may have exceeded one of the lower or upper boundaries for impedance. The exceedances may occur for a certain period of times (e.g. 24 hours, 1 day, 2 days, 3 days, 4 days, 5 days, 6 days, 7 days etc.) At block 1004, a determination is made by the processor as to whether the raw impedance actually exceeded one of the lower or upper boundaries for impedance or the exceedance was due to an artifact. The raw impedance is compared to the reference impedance. For example, OPTIVOL® is triggered (100% arrow) such that the raw impedance is lower than the reference impedance.

At block 1004, a determination is made as to whether impedance was increased due to artifacts. If so, the YES path continues to block 1006 where the process is stopped. Optionally, the patient is advised to visit the clinic to reset the impedance reference. Follow-up transmissions are not programmed into the device because the patient does not require any follow-up.

The NO path from block 1004 continues to block 1008 in which a determination is made as to whether the patient exhibits symptoms. Symptoms not related to worsening HF include worsening COPD, worsening ischemia. In other words, if it is a non-HF related OptiVol crossing, the method is stopped and the method does not proceed with medication intervention.

The YES path from box 1008 to block 1010 indicates that the diuretic should not be increased; rather, the underlying cause of the symptom should be treated. The NO path from block 1008 continues to block 1012 in which a determination is made as to whether the patient's blood pressure is less than 80. If so, the YES path from block 1012 continues to block 1016. The patient is contacted. The patient is directed to stop taking the diuretic and to contact physician for management of blood pressure and any other symptoms.

The NO path from block 1012 continues to block 1014. At block 1014, a determination is made as to whether impedance boundaries have been crossed within a certain amount of time (e.g. previous 3 months etc.) The YES path from block 1014 continues to block 1024. At block 1024, the physician is contacted. The patient's baseline medications may need to be adjusted based upon patient tests results. If the baseline medications are adjusted, the patient's renal functions needs to be checked within a certain amount of time (e.g. 7 days). Follow-up transmissions are programmed in to the device. The NO path from block 1014 continues to block 1018. At block 1018, the patient is asked whether he or she has stopped taking the diuretic. If so, the diuretic reinitiated. The patient should be encouraged to consistently take the proper dosage of the diuretic. If the patient is taking the diuretic, then PRN is initiated. Follow-up transmission (s) are then initiated. For example, the first follow-up transmission can be set at 4 days and the second transmission can be set at 8 days.

At block 1020, a determination is made as to whether the BP is less than 80 or the patients' symptoms worsened. Exemplary HF related symptoms or related to patient's general well-being. For example, a patient can be experiencing dizziness, which will cause the method to be stopped and refer the patient to care team. If either of these conditions has occurred then, the patient may be experiencing dehydration. Any new symptoms that warrant not proceeding with the intervention will also stop the intervention into therapy delivered to a patient. For example, extreme chest pain that did not previously exist earlier can also stop the method.

If the patient has not recovered, the next round of medication is issued. In one embodiment, the patient will only receive two rounds of the medication.

At block 1022, a determination is made as to whether the patient is sufficiently stabilized based upon IMD diagnostic parameter data, weight of the patient, and blood pressure. Weights could be compared with patient baseline weight. BP is vital sign that is tightly regulated and upper and/or lower bounds set. The upper and/or lower bounds can be automatically established for a general population of HF patients or customized to the patient by medical personnel.

The YES path from block 1020 continues to block 1016, which was previously described. The NO path from block 1020 continues to block 1024 in which the diuretic dosage is adjusted (i.e. increased), nitrate delivery is initiated and renal function is checked after a certain time period. Renal function is checked by evaluating electrolytes (e.g. creatinine etc.) in the blood stream within 10 days of modification of the medicine. At block 1026, a determination is made as to whether the patient is stabilized. If so, the YES path continues from block 1026 to block 1028 in which the process is stopped. The NO path continues to block 1028 in which the physician is contacted and information or additional evaluation is performed similar to block 1024. Additionally, the patient is advised to see a physician if his symptoms worsen.

The present disclosure encompasses numerous embodiments as described herein.

Embodiment 1 is a method of operation of a medical system for determining whether a patient is at risk of exhibiting excessive fluid or dehydration, the method comprising:
(a) acquiring from an implantable medical device memory a patient's absolute intrathoracic impedance data over a time period;
(b) determining, through a processor, an average of the intrathoracic impedance data over the time period;
(c) defining, through the processor, a target impedance range bounded by a first range and a second range, the first range being a lower value intrathoracic electrical impedance and the second range being a higher value of intrathoracic electrical impedance; and
(d) determining, through the processor, whether the average of the intrathoracic impedance data is outside one of the first and second ranges.

Embodiment 2 is the method according to embodiment 1 wherein the patient is determined to exhibit excessive fluid in response to determining that the average of intrathoracic impedance data is outside of the target impedance range and extends outside the first range.

Embodiment 3. Is the method according to embodiments 1-2 wherein the patient is determined to be dehydrated in response to determining the average of the intrathoracic impedance data is outside of the target impedance range and outside the second range.

Embodiment 4 is the method according to embodiments 1-3 further comprising:
(e) in response to step d, the processor determines a level of heart failure (HF) event risk based upon whether the average of impedance is outside the targeted impedance range.

Embodiment 5 is the method according to embodiments 1-4 further comprising:
(f) in response to step d, the system performing one of automatically adjusting therapy delivered to a patient.

Embodiment 6 is the method according to embodiments 1-5 further comprising:
(g) generating a notification to one of a patient and health care worker.

Embodiment 7 is the method according to embodiments 1-6 wherein the notification being displayed on a graphical user interface of a device or generated as an alarm.

Embodiment 8 is the method according to embodiments 1-7 wherein the first and second ranges are asymmetrical to each other relative to a target impedance reference.

Embodiment 9 is the method according to embodiments 1-8 wherein the average of the intrathoracic impedance data is a running average.

Embodiment 10 is the method according to embodiments 1-9 wherein the first and second ranges are symmetrical when the first and second ranges are equidistant away, or about equidistant away, from the target impedance reference.

Embodiment 11 is the method according to embodiments 1-10 wherein therapy delivered to the patient is adjusted.

Embodiment 12 is the method according to embodiments 1-11 wherein the therapy is adjusted by switching to one of fusion pacing, biventricular pacing, and multisite pacing.

Embodiment 13 is the method according to embodiments 1-12 wherein medication dosage is adjusted.

Embodiment 14 is the method according to embodiments 1-13 wherein the medication is a diuretic or a nitrate.

Embodiment 15 is the method according to embodiments 1-14 wherein the processor determines risk of a HF event which comprises one of hospitalization for heart failure (HFH), IV, and diuresis.

Embodiment 16 is the method according to embodiments 1-15 wherein HFH comprises one of an emergency room visit and a visit to a clinic.

Embodiment 17 is the method according to embodiments 1-16 wherein the first range extends up to +10% of a baseline mean impedance for a hypovolemia diagnosis and the second range extends up to −10% for a hypervolemia diagnosis.

Embodiment 18 is a medical system for determining prospective heart failure event risk, the system comprising:
processing means for determining whether a patient is at risk of hypervolemia, the method comprising:
(a) acquiring from a device memory a patient's absolute intrathoracic impedance data over a pre-specified time period;
(b) means for determining a running average of the intrathoracic impedance data over the pre-specified time period; and (c) means for determining by the system whether the running average of the intrathoracic impedance data over the pre-specified time period is out-of-range from one of a first and second range, the first range being a higher value boundary of intrathoracic electrical impedance and the second range being a lower value boundary of intrathoracic electrical impedance.

Embodiment 19 is the system according to embodiment 18 further comprising:

(d) in response to step c, the system determines level of heart failure event risk based upon whether the moving average of impedance is outside of the targeted impedance range.

Embodiment 20 is the system according to embodiments 18-19 further comprising:

(e) in response to step c, the system performing one of automatically adjusting therapy delivered to a patient and generating a notification to one of a patient and health care worker.

Embodiment 21 is the system according to embodiments 18-20 wherein one of the first and second ranges are asymmetrical relative to the target impedance range such that either the first range or the second range is closer to the target impedance reference.

Embodiment 22 is the system according to embodiments 18-21 wherein the patient is determined to exhibit excessive fluid in response to determining that the average of intrathoracic impedance data is outside of the target impedance range and extends beyond the first range.

Embodiment 23 is the system according to embodiments 18-22 wherein the patient is determined to be dehydrated in response to determining the average of the intrathoracic impedance data is outside of the target impedance range and extends away from the second range.

Embodiment 24 is the system of embodiment 18-24 wherein decreased intrathoracic impedance causes the average intrathoracic impedance to go outside the lower boundary indicating the patient is experiencing hypervolemia.

Embodiment 25 is a method of operation of a medical system for determining whether a patient is at risk of exhibiting hypovolemia or hypervolemia, the method comprising:

(a) acquiring from an implantable medical device memory a patient's absolute intrathoracic impedance data;
(b) determining, through a processor, an average of the intrathoracic impedance data;
(c) defining, through the processor, a target impedance range bounded by a first range and a second range, the first range being a lower value intrathoracic electrical impedance and the second range being a higher value of intrathoracic electrical impedance; and
(d) determining, through the processor, whether the average of the intrathoracic impedance data is outside one of the first and second ranges.

Thus, various embodiments of an IMD system and method for closed loop adjustment of a therapy delivery has been described. However, one of ordinary skill in the art will appreciate that various modifications may be made to the described embodiments without departing from the scope of the claims.

The invention claimed is:

1. A medical system for determining whether a patient is at risk of exhibiting excessive fluid or dehydration and for delivering treatment in response thereto, the system comprising:

an implantable medical device having a device memory storing a patient's absolute intrathoracic impedance data over a time period, the implantable medical device comprising:
a plurality of electrodes; and
a processor configured to:
(a) determine an average of the absolute intrathoracic impedance data over the time period, wherein the absolute intrathoracic impedance data comprises raw impedance data measured between two electrodes of the plurality of electrodes, and wherein the average comprises a moving average;
(b) define a target impedance range having a lower bound and an upper bound, the lower bound defining a lower value intrathoracic electrical impedance and the upper bound defining a higher value intrathoracic electrical impedance;
(c) determine whether the average of the absolute intrathoracic impedance data is outside of the target impedance range; and
(d) in response to the average of the absolute intrathoracic impedance data being outside the target impedance range, determine a level of heart failure (HF) event risk;
(f) in response to step (d), instruct the implantable medical device to adjust therapy delivered to the patient wherein the therapy is adjusted by switching to one of fusion pacing, biventricular pacing, and multisite pacing delivered by the implantable medical device.

2. The system of claim 1 wherein the processor determines that the patient exhibits excessive fluid in response to determining that the average of the absolute intrathoracic impedance data is below the lower bound.

3. The system of according to claim 1 wherein the processor determines that the patient exhibits dehydration in response to determining that the average of the absolute intrathoracic impedance data is above the upper bound.

4. The system of claim 1 wherein the processor is further configured to generate and transmit a notification to one of a patient and health care worker in response to determining that the average of the absolute intrathoracic impedance data is outside the target impedance range.

5. The system of claim 4 further comprising a graphical user interface configured to receive and display the notification.

6. The system of claim 5 wherein the graphical user interface is further configured to trigger an alarm in response to receiving the notification.

7. The system of claim 1 wherein the upper bound and the lower bound are asymmetrical relative to a defined target impedance reference within the target range.

8. The system of claim 1 wherein the upper bound and the lower bound are symmetrical relative to a defined target impedance reference within the target range.

9. The system of claim 1, wherein the processor is further configured to generate a notification indicating to adjust a delivery of a medication, wherein the medication is a diuretic or a nitrate.

10. The system of claim 1 wherein the processor determines risk of a HF event which comprises one of hospitalization for heart failure (HFH) and intravenous diuresis.

11. The system of claim 10 wherein HFH comprises one of an emergency room visit and a visit to a clinic.

12. The system of claim 1 wherein the average of the absolute intrathoracic impedance data over the time period comprises the moving average of the absolute intrathoracic impedance data over a period of 10 days or less.

\* \* \* \* \*